United States Patent
Wang et al.

(10) Patent No.: US 7,629,480 B2
(45) Date of Patent: Dec. 8, 2009

(54) ORGANIC ACID ANION CONTAINING ALUMINUM SALT HYDROXIDE PARTICLES, PRODUCTION METHOD THEREOF, AND USE THEREOF

(75) Inventors: Xing Dong Wang, Sakaide (JP); Akira Okada, Sakaide (JP)

(73) Assignee: Kyowa Chemical Industry Co., Ltd., Kagawa (JP)

( * ) Notice: Subject to any disclaimer, the term of this patent is extended or adjusted under 35 U.S.C. 154(b) by 50 days.

(21) Appl. No.: 10/591,588

(22) PCT Filed: Mar. 1, 2005

(86) PCT No.: PCT/JP2005/003831

§ 371 (c)(1),
(2), (4) Date: Sep. 5, 2006

(87) PCT Pub. No.: WO2005/085168

PCT Pub. Date: Sep. 15, 2005

(65) Prior Publication Data

US 2007/0189986 A1 Aug. 16, 2007

(30) Foreign Application Priority Data

Mar. 5, 2004 (JP) .............................. 2004-062549

(51) Int. Cl.
- *C09B 67/00* (2006.01)
- *C01F 7/02* (2006.01)
- *C01F 7/34* (2006.01)
- *A61Q 17/04* (2006.01)
- *C07F 5/06* (2006.01)
- *C07C 55/06* (2006.01)

(52) U.S. Cl. .................. 556/27; 106/402; 423/600; 424/59; 562/597

(58) Field of Classification Search .......... 106/402; 423/600; 424/59; 556/27; 562/597
See application file for complete search history.

(56) References Cited

U.S. PATENT DOCUMENTS

| | | | |
|---|---|---|---|
| 3,903,240 A * | 9/1975 | Lopez | .......... 423/127 |
| 5,461,082 A | 10/1995 | Machimura et al. | |
| 6,548,689 B1 * | 4/2003 | Pratt, III | .......... 556/183 |
| 6,706,249 B1 | 3/2004 | Komatsu et al. | |
| 2006/0068289 A1 * | 3/2006 | Paulsen et al. | .......... 429/231.1 |

FOREIGN PATENT DOCUMENTS

| | | |
|---|---|---|
| JP | 64-11637 | 1/1989 |
| JP | 64-11638 | 1/1989 |
| JP | 6-122519 | 5/1994 |
| JP | 8-41076 | 2/1996 |
| JP | 10-273324 | 10/1998 |
| JP | 2000-7326 | 1/2000 |
| WO | 01/04053 | 1/2001 |

OTHER PUBLICATIONS

English abstract and computer translation of JP 2007-039442 published Feb. 15, 2007.
European Search Report dated Jan. 31, 2008 in European Application No. 05 72 0103 corresponding to the present U.S. application.
Komatsu, Yoshinobu et al., "Preparation of composite metal polybasic salts by sulfate anion exchange of complex metal polybasic sulfate particles", XP002465070, retrieved from STN Database accession No. 2002:63384 & JP 2002 020121 A (Mizusawa Industrial Chemicals, Ltd., Japan), Jan. 23, 2002.
Motoharu Kawano et al., "Syntheses and High Temperature Phase Transformations of Alunite-Natroalunite Solid Solution Series", Mineralogy Journal, vol. 20, No. 1 and 2, pp. 13-23, Jan. and Apr. 1991.
Katsuya Inouye et al., "The High-order Structure and Dye Adsorption of a Porous Alunite", Journal of Chemical Society of Japan, (2), pp. 156-162, 1985.

* cited by examiner

*Primary Examiner*—Peter G O'Sullivan
(74) *Attorney, Agent, or Firm*—Wenderoth, Lind & Ponack, L.L.P.

(57) ABSTRACT

There are provided organic acid anion containing aluminum salt hydroxide particles represented by the following general formula (I):

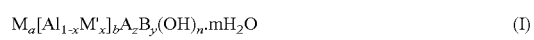

$$M_a[Al_{1-x}M'_x]_b A_z B_y(OH)_n \cdot mH_2O \qquad (I)$$

(wherein M is at least one cation selected from the group consisting of $Na^+$, $K^+$, $NH^{4+}$ and $H_3O^+$, M' is at least one metal cation selected from the group consisting of $Cu^{2+}$, $Zn^{2+}$, $Ni^{2+}$, $Sn^{4+}$, $Zr^{4+}$, $Fe^{2+}$, $Fe^{3+}$ and $Ti^{4+}$, A is at least one organic acid anion, B is at least one inorganic acid anion, and a, b, m, n, x, y and z satisfy $0.7 \leq a \leq 1.35$, $2.7 \leq b \leq 3.3$, $0 \leq m \leq 5$, $4 \leq n \leq 7$, $0 \leq x \leq 0.6$, $1.7 \leq y \leq 2.4$, and $0.001 \leq z \leq 0.5$, respectively.)

The particles are in the shape of grains, pairs, rectangular parallelepiped, disks (go stones), hexagonal plates, rice grains or cylinders and have a uniform particle diameter.

18 Claims, 16 Drawing Sheets

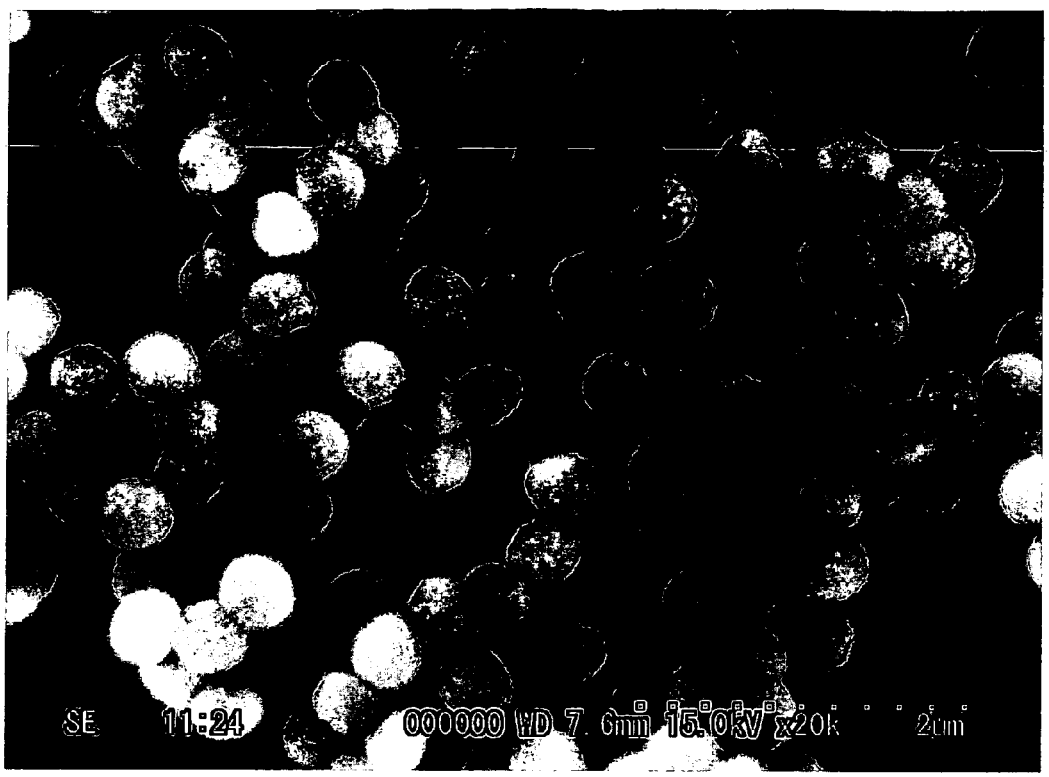
FIG. −1
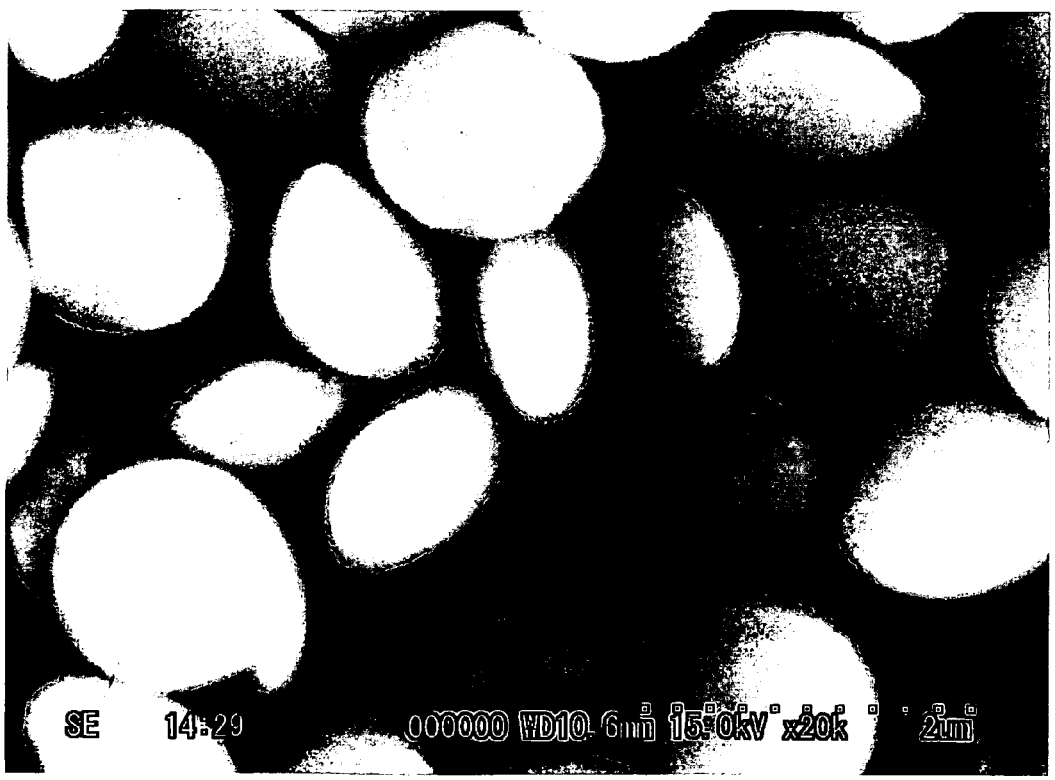
FIG. −2

FIG. −11

ORGANIC ACID ANION CONTAINING ALUMINUM SALT HYDROXIDE PARTICLES, PRODUCTION METHOD THEREOF, AND USE THEREOF

BACKGROUND OF THE INVENTION (i) Field of the Invention

The present invention relates to organic acid anion containing aluminum salt hydroxide particles, a production method thereof, and use thereof. That is, the present invention relates to organic acid anion containing aluminum salt hydroxide particles which can be used in various fields, such as fields of construction, food, agriculture, semiconductors, electrophotography, medical care, cosmetics, chemical, resins, fibers and rubber, and other industrial fields, and a production method of the particles. More specifically, the present invention relates to organic acid anion containing aluminum salt hydroxide particles which have a very small and uniform particle diameter, are in the shape of spheres, pairs, rectangular parallelepiped, disks (go stones), hexagonal plates, rice grains or cylinders and have low moisture absorbability and excellent addability to rubber or the like, and to a production method of the particles and use of the particles.

(ii) Description of the Related Art

A representative alunite compound is alunite. Natural alunite exists as alumstone in heat mineral deposits and acid-corroded areas formed by active volcanoes or hot springs. Synthetic alunite is used in the industry as an adsorbent, an additive to resins, a filler and various carriers. The following synthetic methods are known.

Publication 1 describes a method for synthesizing alumstone by mixing aluminum sulfate ($Al_2(SO_4)_3$), potassium sulfate ($K_2SO_4$) and sodium sulfate ($Na_2SO_4$) in a given ratio and agitating the mixture continuously at 100° C. under atmospheric pressure for 48 hours by a magnetic stirrer equipped with a hot plate.

Publication 2 describes a method for producing alunite having a specific surface area of 200 to 240 m²/g by adding potassium sulfate ($K_2SO_4$) and potassium hydroxide (KOH) to an aluminum sulfate ($Al_2(SO_4)_3$) aqueous solution to adjust the K/Al ratio to 5 and the pH to 3.7 and boiling and refluxing the solution for three hours. It has been reported that alunite produced by this method is a flake-shaped porous aggregate which has slits having a width of 15 to 30 Å and has water adsorbability comparable to that of silica gel and high adsorbability to $SO_2$ and NO and adsorbs acidic dyes well.

Publication 1: Kawano et al., Mineralogy Journal, Vol. 20, Num. 1 and 2, pp. 13 to 23, January and April, 1991

Publication 2: Inoue et al., Journal of Chemical Society of Japan, 1985(2), pp. 156 to 162

As methods for producing alunite compounds at low cost and in good yield to use them as adsorbents in the industry, the following Publications 3, 4 and 5 are known.

Publication 3 (JP-A 64-11637 (the term "JP-A" as used herein means an "unexamined published Japanese patent application") describes an alunite type adsorbent represented by the following formula:

$$MM'_3(SO_4)_2(OH)_6$$

(wherein M represents a monovalent cation, and M' represents Al or a combination of Al and Fe(III)), and having a BET specific surface area of not smaller than 280 m²/g and a pore volume within a pore diameter of 100 to 300 Å of not smaller than 0.05 ml/g. As for synthesis thereof, a method in which when aluminum sulfate or a combination of aluminum sulfate and ferric sulfate and alkali sulfate are subjected to a heating reaction in an aqueous solvent containing alkali hydroxide, the pH of the reaction solution is kept at 4.0 to 4.4 from the start of the reaction and the pH of the reaction is kept at 3.8 or higher in the reaction process so as to crystallize an alunite type layered compound having an increased specific surface area is described.

Publication 4 (JP-A 64-11638) describes an adsorbent composition that comprises a homogeneous composition comprising a layered compound having a chemical structure represented by the following formula:

$$MM'_3(SO_4)_2(OH)_6$$

(wherein M represents a monovalent cation, and M' represents Al or Fe(III)), and an alunite type or jarosite type crystal structure and amorphous silica or amorphous silica alumina whose amount is 5 to 80 wt % based on the layered compound and that has a BET specific surface area of not smaller than 300 m²/g and a pore volume of not smaller than 0.1 ml/g. Further, it is described with respect to a production method thereof that alunite type and jarosite type layered compounds can be crystallized depending on starting materials and the value of pH in the reaction.

Publication 5 (JP-A 2000-7326) describes a spindle-shaped or spherical alkali aluminum salt hydroxide that comprises independent particles, is represented by the following formula:

$$MAl_3(SO_4)_2(OH)_6$$

(wherein M is a monovalent alkali metal or an ammonium group), $D_{25}$ and $D_{75}$ satisfy:

$$1.2 \leq D_{75}/D_{25} \leq 2$$

when particle diameters at 25% and 75% values of volume-based cumulative particle size distribution curve by a Coulter method are represented by $D_{25}$ and $D_{75}$, respectively, and is specified by chemical composition, and X-ray diffraction images, the pH of 5% aqueous suspension, a BET specific surface area and moisture absorbability which are different from those of alunite. Further, in this publication, an alkali aluminum salt hydroxide whose parameters such as the bulk specific gravity of particles, a volume-based median diameter, the degree of sharpness of particle size distribution, an aspect ratio, a refractive index and the degree of abrasion are optimum with respect to compatibility with resins is proposed. As for a production method thereof, it is described that aluminum sulfate, alkali sulfate or ammonium sulfate and aluminum hydroxide are subjected to a hydrothermal treatment. Further, a method of controlling the shape of particles to either a sphere or a spindle is also suggested.

Meanwhile, Publication 6 (JP-A 6-122519) discloses a method for synthesizing "jarosite particles (amorphous water-containing ferric oxide particle powder)" which have spherical shapes, have an average particle diameter of 3 to 30 μm, a specific surface area BET value of 150 to 300 m²/g and a bulk density of 0.7 to 1.1 g/ml and are represented by the following formula:

$$RFe_3(SO_4)_2(OH)_6 \text{ (R is } K^+, Na^+, NH_4^+ \text{ or the like.)}$$

This publication proposes repetitive use of reaction mother liquor, i.e., "jarosite particles are produced by passing oxygen-containing gas through a mixed solution of a ferrous sulfate solution and a sulfate solution of alkali metal or ammonium ions to carry out an oxidation reaction within a temperature range of higher than 45° C. and not higher than the boiling point."

SUMMARY OF THE INVENTION

Problems to be Solved by the Invention

It is proposed in the above Publications 2 and 3 to 5 that a synthetic alunite compound can be used as an additive or a filler to resin, rubber and the like, an adsorbent for odorous components, or a carrier for dyes and the like. In general, when the synthetic alunite compound is used as an additive or a filler to resins, rubber and the like, it is needless to say that the compound should have low moisture absorbability, high acid resistance and good dispersibility to minimize deterioration in mechanical properties such as tensile strength; however, in addition to these properties, transparency (total light transmittance becomes higher and haze becomes thinner as particle diameters become smaller) and a constant particle shape and a uniform particle diameter (sharpness of particle size distribution) for the closest filling are often required depending on applications. In addition, when the synthetic alunite compound is mixed into a resin, the compound is required to have a uniform particle diameter to reduce the frequency of occurrence of clogging of a filter and to improve processability in processing the mixture into fine fibers and the like. To satisfy these requirements, it is requested that the particle diameter be reduced and the particle shape and the uniform particle diameter be ensured without degrading dispersibility into resins. The above requirements contradict each other, and there is a problem that when the particle diameter is reduced to improve mechanical properties and transparency, secondary flocculation is liable to occur, so that dispersibility into resins, rubber and the like deteriorates, thereby causing deterioration in the mechanical properties and transparency. The composition described in the above Publication 2 has so high moisture absorbability that it cannot be used as an additive to resins, rubber and the like. The above Publications 3, 4 and 6 do not disclose methods for securing a particle shape, a uniform particle diameter, and these properties, and compatibility or dispersibility into a resin or retainability of mechanical properties such as tensile strength are unknown. Meanwhile, the above Publication 5 suggests a method for controlling a particle shape to either a sphere or a spindle by controlling pH in a reaction. This method is incomplete and is an unrealistic and uneconomical method particularly when a heating reaction at high temperatures is involved, because alkali hydroxide as a pH adjuster must be added while pH is measured at given time intervals during the reaction. Further, Publication 5 does not mention methods for controlling a particle diameter and particle size distribution which are important parameters. Shaped particles disclosed in Publication 5 show relatively great variations in particle diameters as indicated by the value of $D_{25}/D_{75}$ which represents uniformity of particle diameter being higher than 1.45 and show an actually obtained average particle diameter of not smaller than about 2 µm.

Meanwhile, when the synthetic alunite compound is used as an adsorbent or a carrier, water absorbability must be as low as possible. In this regard, the composition described in the above Publication 2 has so high moisture absorbability that gas adsorbability deteriorates in an environment where relative humidity is high. Further, adsorbents and carriers for industrial use are often used in a strongly acidic environment and are required to have acid resistance. Accordingly, a change in crystal structure associated with adsorption and carrying in the strongly acidic environment is required to be as small as possible. However, acid resistance is not described at all in any of the above Publications 3 to 6.

The first object of the present invention is to provide organic acid anion containing aluminum salt hydroxide particles having a uniform particle shape and a uniform particle diameter. The second object of the present invention is to provide organic acid anion containing aluminum salt hydroxide particles having novel shapes which have not been known. The third object of the present invention is to provide organic acid anion containing aluminum salt hydroxide particles having various excellent properties, e.g., having excellent adsorbability to alkali substances, not losing the functions in a strongly acidic environment, having good dispersibility into a resin, rubber or the like and good moldability, not deteriorating the physical properties of the resin, rubber or the like even when dispersed therein in high density, and not deteriorating the flowability of coating material or the like even when added to the coating material or the like. The fourth object of the present invention is to provide a method for producing organic acid anion containing aluminum salt hydroxide particles having a desired particle shape and a uniform particle diameter. The fifth object of the present invention is to provide an adsorbent, an ultraviolet absorber and a resin composition which use the above organic acid anion containing aluminum salt hydroxide particles.

Means for Solving the Problems

The present inventors have obtained the unexpected result that organic acid anion containing aluminum salt hydroxide particles that show particle size uniformity which has not heretofore been achieved and have a rectangular parallelepiped shape can be synthesized by adding oxalic acid ($C_2H_2O_4$) to a mixed solution in a known synthesis method of alunite compound particles in which a sodium hydroxide solution is added to the mixed solution comprising aluminum sulfate and sodium sulfate as a catalyst to cause a heating reaction as disclosed in the above Publication 5.

Further, the present inventors have found that organic acid anion containing aluminum salt hydroxide particles showing very high uniformity in particle size and having a spherical shape and a smooth particle surface can be synthesized by adding potassium hydroxide to a mixed solution comprising aluminum sulfate, potassium sulfate and oxalic acid.

The present inventors have developed studies based on a number of experiments using the above findings as clues. As a result, they have found that organic acid anion containing aluminum salt hydroxide particles that have various shapes which have not been attained by a conventional method and particle size uniformity and are represented by the following formula (I) can be synthesized by adding a given amount of an organic acid to a mixed solution in a known synthesis method of aluminum salt hydroxide particles in which an alkali hydroxide solution containing a monovalent cation is added to the mixed solution comprising a sulfate of a trivalent metal and a sulfate of the monovalent cation as a catalyst to cause a heating reaction.

Further, the present inventors have also found that organic acid anion containing aluminum salt hydroxide particles having a desired particle diameter and a desired particle shape according to applications can be obtained by changing the kind of the alkali hydroxide to be added or the kind of organic acid or organic acid salt in particular. More specifically, organic acid anion containing aluminum salt hydroxide particles can be obtained which are in the shape of not only a sphere but also a pair, a rectangular parallelepiped, a disk (go stone), a rice grain or a cylinder. To the best of the present inventors' knowledge, organic acid anion containing aluminum salt hydroxide particles, i.e., complex particles comprising an organic acid and an alunite type compound, are novel.

In the present invention, the novel organic acid anion containing aluminum salt hydroxide particles are represented by the following formula (I):

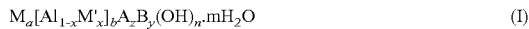
$$M_a[Al_{1-x}M'_x]_b A_z B_y(OH)_n \cdot mH_2O \quad (I)$$

wherein M is at least one cation selected from the group consisting of $Na^+$, $K^+$, $NH_{4+}$ and $H_3O^+$, and M' is at least one cation selected from the group consisting of $Cu^{2+}$, $Zn^{2+}$, $Ni^{2+}$, $Sn^{4+}$, $Zr^{4+}$, $Fe^{2+}$, $Fe^{3+}$ and $Ti^{4+}$.

A is at least one organic acid anion, preferably at least one selected from anions based on an organic carboxylic acid and an organic oxycarboxylic acid, more preferably at least one selected from anions based on an organic carboxylic acid and an organic oxycarboxylic acid which have 1 to 15 carbon atoms. A is much more preferably at least one selected from anions based on an organic carboxylic acid and an organic oxycarboxylic acid which have 1 to 15 (particularly 2 to 10) carbon atoms and 1 to 4 (preferably 1 or 2) carboxyl groups, particularly preferably at least one selected from the group consisting of an oxalate ion, a citrate ion, a malate ion, a tartrate ion, a glycerate ion, a gallate ion, and a lactate ion.

B is at least one inorganic acid anion, preferably at least one selected from inorganic acid anions having a tetrahedron structure, more preferably at least one selected from the group consisting of a sulfate ion ($SO_4^{2-}$), a phosphate ion ($PO_4^{3-}$), a nitrate ion ($NO_3^{1-}$) and a silicate ion ($SiO_3^{2-}$, $SiO_4^{4-}$, $HSi_2O_5^-$ and the like), much more preferably at least one selected from a sulfate ion, a phosphate ion and a silicate ion, most preferably a sulfate ion.

Further, a, b, n, m, x, y and z in the formula satisfy $0.7 \leq a \leq 1.35$, $2.7 \leq b \leq 3.3$, $0 \leq m \leq 5$, $4 \leq n \leq 7$, $0 \leq x \leq 0.6$, $1.7 \leq y \leq 2.4$ and $0.001 \leq z \leq 0.5$, preferably $0.9 \leq a \leq 1.2$, $2.8 \leq b \leq 3.2$, $0 \leq m \leq 2$, $5 \leq n \leq 6.5$, $0 \leq x \leq 0.3$, $1.8 \leq y \leq 2.2$ and $0.01 \leq z \leq 0.4$, more preferably $0.9 \leq a \leq 1.2$, $2.8 \leq b \leq 3.2$, $0 \leq m \leq 2$, $5 \leq n \leq 6.5$, $0 \leq x \leq 0.3$, $1.8 \leq y \leq 2.2$ and $0.05 \leq z \leq 0.3$, much more preferably $3.6 \leq a+b \leq 4.4$, $0 \leq m \leq 2$, $5 \leq n \leq 6.5$, $0 \leq x \leq 0.3$ and $1.7 \leq y+z \leq 2.4$, particularly preferably $3.6 \leq a+b \leq 4.4$, $0 \leq m \leq 2$, $5 \leq n \leq 6.5$, $0 \leq x \leq 0.3$ and $1.8 \leq y+z \leq 2.2$, most preferably $3.6 \leq a+b \leq 4.4$, $0 \leq m \leq 2$, $0 \leq x \leq 0.3$ and $7.5 \leq y+n \leq 8.5$.

Thus, according to the present invention, the following organic acid anion containing aluminum salt hydroxide particles, a production method thereof and use thereof are provided.

(1) Organic acid anion containing aluminum salt hydroxide particles represented by the following general formula (I):

$$M_a[Al_{1-x}M'_x]_b A_z B_y(OH)_n \cdot mH_2O \quad (I)$$

(wherein M is at least one cation selected from the group consisting of $Na^+$, $K^+$, $NH^{4+}$ and $H_3O^+$, M' is at least one metal cation selected from the group consisting of $Cu^{2+}$, $Zn^{2+}$, $Ni^{2+}$, $Sn^{4+}$, $Zr^{4+}$, $Fe^{2+}$, $Fe^{3+}$ and $Ti^{4+}$, A is at least one organic acid anion, B is at least one inorganic acid anion, and a, b, m, n, x, y and z satisfy $0.7 \leq a \leq 1.35$, $2.7 \leq b \leq 3.3$, $0 \leq m \leq 5$, $4 \leq n \leq 7$, $0 \leq x \leq 0.6$, $1.7 \leq y \leq 2.4$, and $0.001 \leq z \leq 0.5$, respectively.)

(2) The particles according to the above (1), which are represented by the above formula (I) wherein a satisfies $0.9 \leq a \leq 1.2$.

(3) The particles according to the above (1), which are represented by the above formula (I) wherein b satisfies $2.8 \leq b \leq 3.2$.

(4) The particles according to the above (1), which are represented by the above formula (I) wherein m satisfies $0 \leq m \leq 2$.

(5) The particles according to the above (1), which are represented by the above formula (I) wherein n satisfies $5 \leq n \leq 6.5$.

(6) The particles according to the above (1), which are represented by the above formula (I) wherein x satisfies $0 \leq x \leq 0.3$.

(7) The particles according to the above (1), which are represented by the above formula (I) wherein y satisfies $1.8 \leq y \leq 2.2$.

(8) The particles according to the above (1), which are represented by the above formula (I) wherein z satisfies $0.01 \leq z \leq 0.4$.

(9) The particles according to the above (1), wherein the organic acid anion (A) in the above formula (I) is at least one selected from anions based on an organic carboxylic acid and an organic oxycarboxylic acid.

(10) The particles according to the above (1), wherein the organic acid anion (A) in the above formula (I) is at least one selected from anions based on an organic carboxylic acid and an organic oxycarboxylic acid which have 1 to 15 carbon atoms.

(11) The particles according to the above (1), wherein the inorganic acid anion (B) in the above formula (I) is at least one selected from the group consisting of a sulfate ion, a phosphate ion, a nitrate ion and a silicate ion.

(12) The particles according to the above (1), wherein the inorganic acid anion (B) in the above formula (I) is a sulfate ion or a sulfate ion and a phosphate ion.

(13) The particles according to the above (1), wherein $D_{25}$ and $D_{75}$ satisfy $1 < D_{75}/D_{25} < 1.8$ when particle diameters at 25% and 75% values of cumulative particle size distribution curve measured by a laser diffraction method are represented by $D_{25}$ and $D_{75}$, respectively.

(14) The particles according to the above (1), which are in the shape of grains, pairs, rectangular parallelepiped, disks (go stones), hexagonal plates, rice grains or cylinders.

(15) The particles according to the above (1), having an average particle diameter of 0.1 to 10 μm.

(16) A burned product obtained by burning the particles of the above (1) at 300 to 1,000° C.

(17) The particles according to the above (1), which carry a hydrolysate of a salt of at least one metal selected from the group consisting of Cu, Zn, Ni, Sn, Zr, Fe and Ti, on the surfaces thereof.

(18) The alunite type compound particles of the above (1), having surfaces thereof treated with at least one surface treating agent selected from the group consisting of a higher fatty acid, an anionic surfactant, a phosphoric ester, a coupling agent, and an ester of a polyhydric alcohol and a fatty acid.

(19) A method for producing organic acid anion containing aluminum salt hydroxide particles, comprising carrying out a heating reaction in the presence of an organic acid or organic acid salt when an alkali hydroxide solution selected from the second group is added to a mixed solution comprising an inorganic salt of $Al^{3+}$ or at least one cation selected from the group consisting of $Al^{3+}$, $Cu^{2+}$, $Zn^{2+}$, $Ni^{2+}$, $Sn^{4+}$, $Zr^{4+}$, $Fe^{2+}$, $Fe^{3+}$ and $Ti^{4+}$ (the first group) and a sulfate or nitrate of at least one cation selected from the group consisting of $Na^+$, $K^+$, $NH_4^+$ and $H_3O^+$ (the second group) to cause the heating reaction.

(20) The method according to the above (19), wherein the above inorganic salt is aluminum sulfate.
(21) The method according to (19), wherein the organic acid is at least one selected from the group consisting of an organic carboxylic acid, an organic oxycarboxylic acid, and their salts.
(22) The method according to the above (19), wherein the organic acid is at least one selected from the group consisting of an organic carboxylic acid having 1 to 15 carbon atoms, an organic oxycarboxylic acid having 1 to 15 carbon atoms, and their salts.
(23) The method according to the above (19), wherein the inorganic acid salt is at least one selected from the group consisting of a sulfate, a nitrate, a phosphate and a silicate.
(24) The method according to the above (19), comprising carrying out the heating reaction at 90 to 250° C.
(25) A resin additive comprising the particles of the above (1).
(26) A resin composition containing the resin additive of the above (25).
(27) An adsorbent composition containing the particles of the above (1).
(28) A dye carrier containing the particles of the above (1).
(29) An ultraviolet absorber containing the particles of the above (1).

BRIEF DESCRIPTION OF THE DRAWINGS

FIG. 1 is an SEM photograph of spherical particles of Example 1-A.
FIG. 2 is an SEM photograph of disk-shaped particles of Example 1-B.

DETAILED DESCRIPTION OF THE PREFERRED EMBODIMENTS

Hereinafter, the organic acid anion containing aluminum salt hydroxide particles of the present invention will be further described.

As for the shapes of aluminum salt hydroxide particles, spindle-shaped particles and spherical particles have been known as described in Publication 5. According to the present invention, organic acid anion containing aluminum salt hydroxide particles are provided which have a new particle shape, e.g., sphere disk (go stone), pairs, rectangular parallelepiped, hexagonal plate, rice grain or cylinder having sharper particle size distribution ($D_{75}/D_{25}$), i.e., a uniform particle diameter. The particles having these new shapes of the present invention are characterized in that they have good shape uniformity (i.e., they have a uniform shape). Further, the particles of the present invention show low tendency of cohesiveness and excellent dispersibility, regardless of shapes thereof and in spite of small particle diameters thereof. The characteristics of the above particle shapes of the organic acid anion containing aluminum salt hydroxide particles of the present invention can also be recognized from the attached FIGS. 1 to 11.

Figure 3:
FIG. 3 is an SEM photograph of paired particles of Example 1-C.
Figure 4:
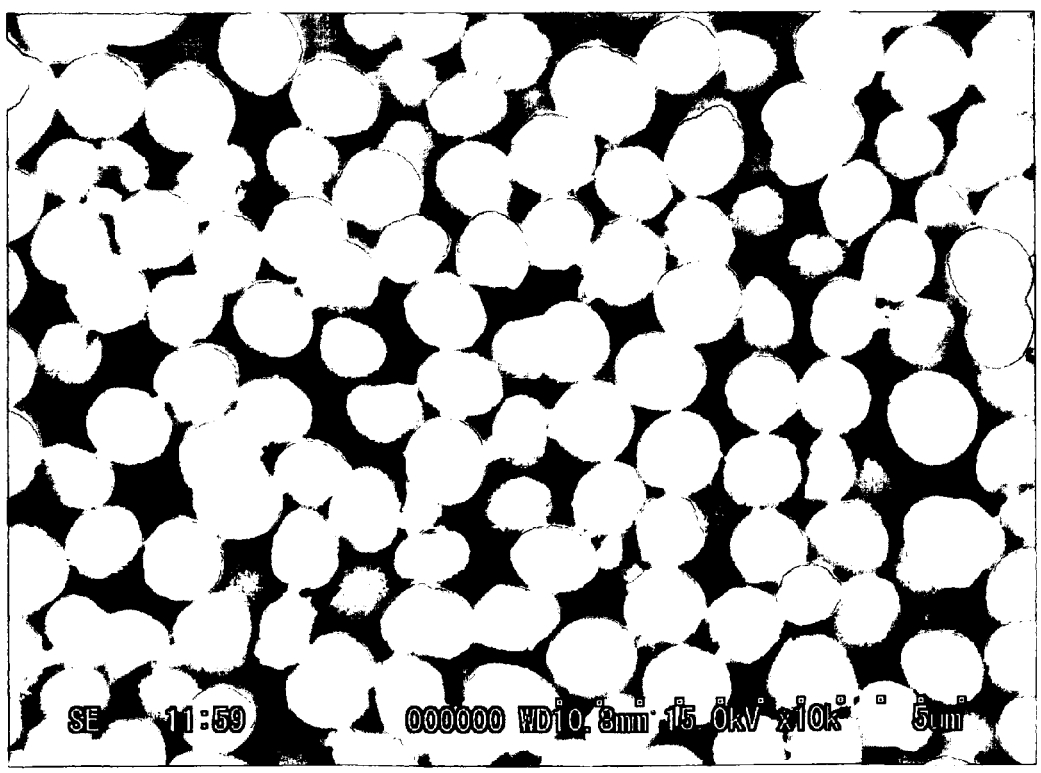
FIG. 4 is an SEM photograph of spherical particles of Example 1-D.
Figure 5:
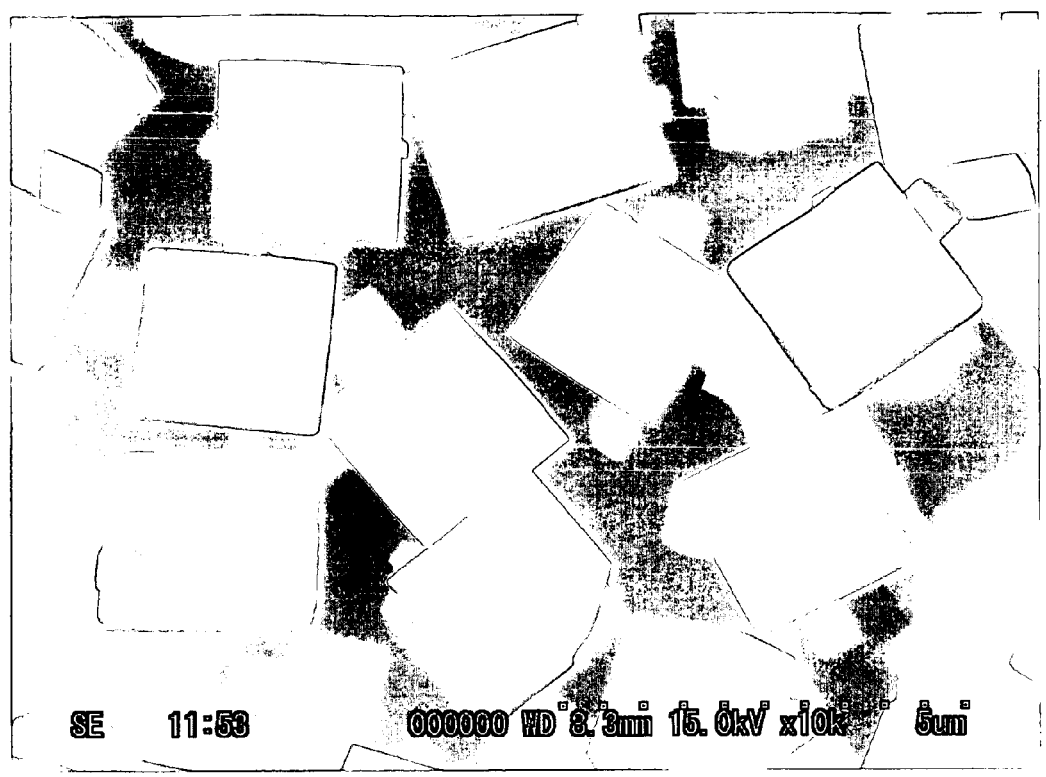
FIG. 5 is an SEM photograph of rectangular-parallelepiped-shaped particles of Example 1-E.
Figure 6:
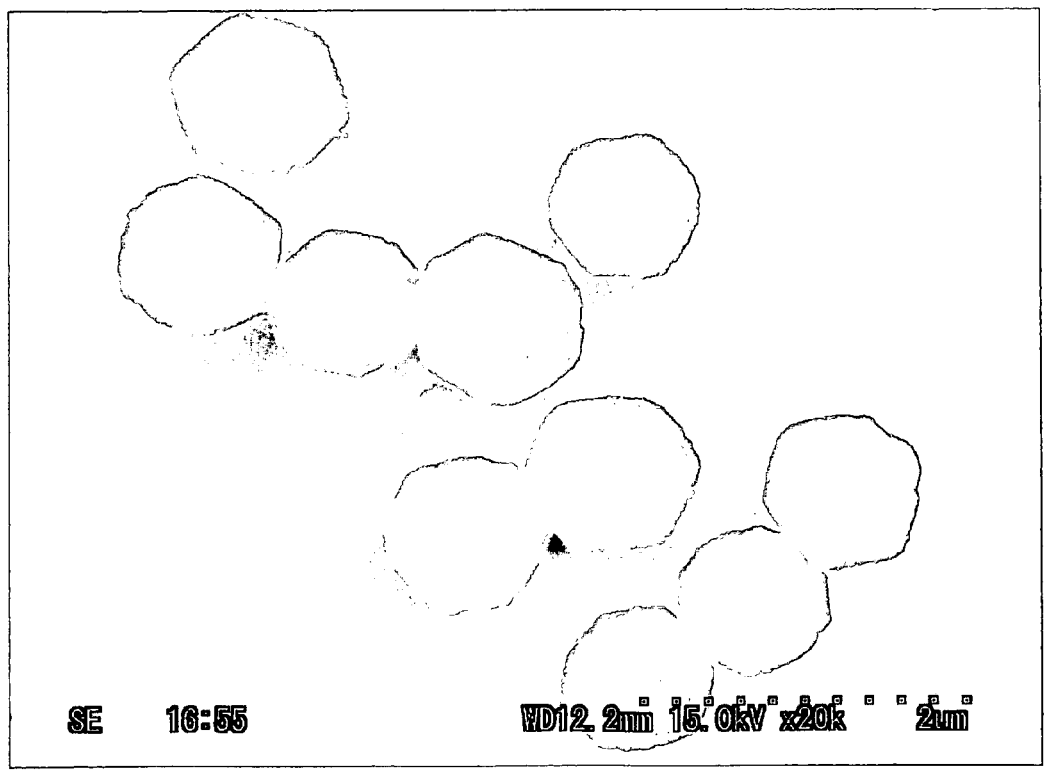
FIG. 6 is an SEM photograph of hexagonal-plate-shaped particles of Example 1-F.
Figure 7:
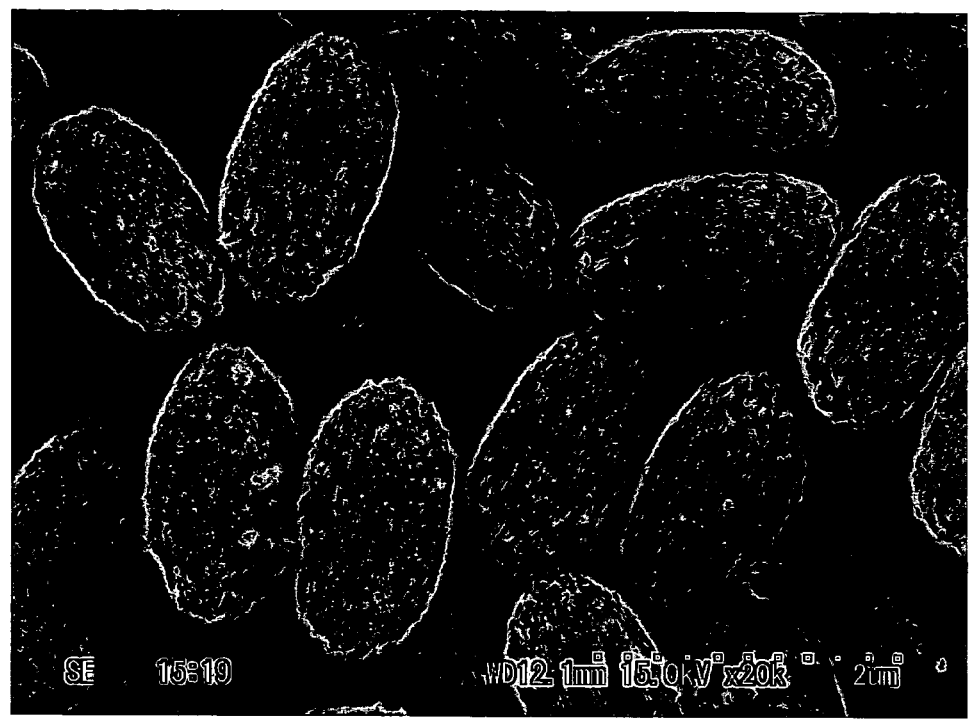
FIG. 7 is an SEM photograph of rice-grain-shaped particles of Example 1-J.
Figure 8:
FIG. 8 is an SEM photograph of cylindrical particles of Example 1-O.
Figure 9:
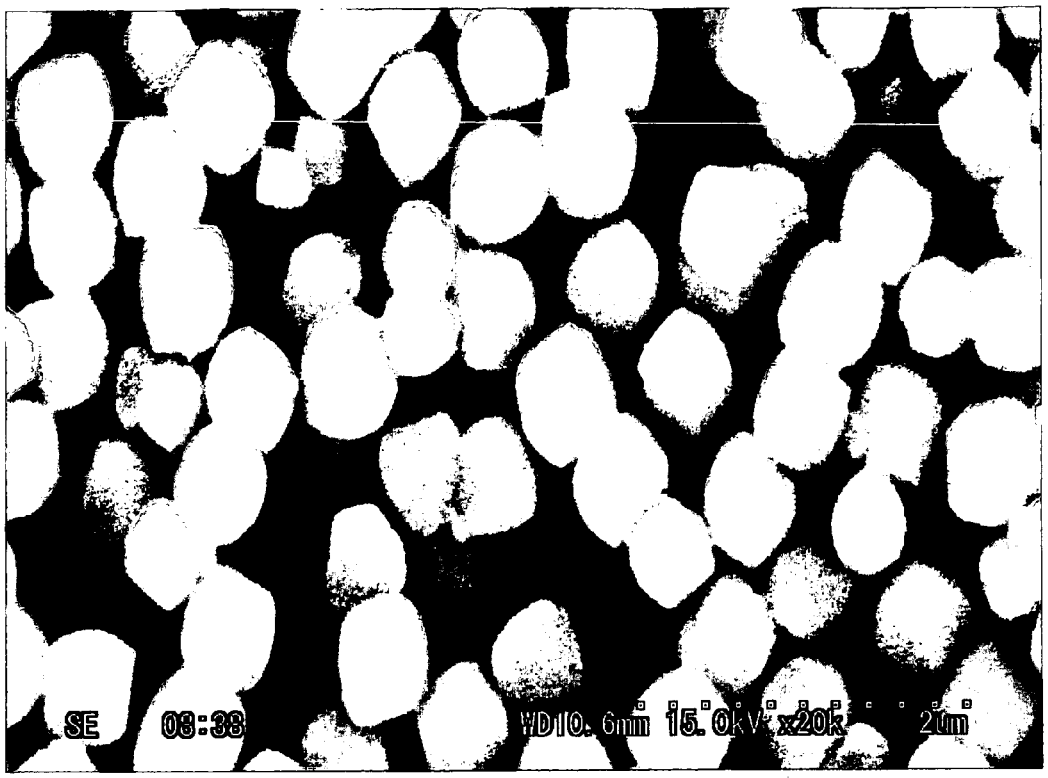
FIG. 9 is an SEM photograph of rectangular-parallelepiped-shaped particles of Example 1-P.
Figure 10:
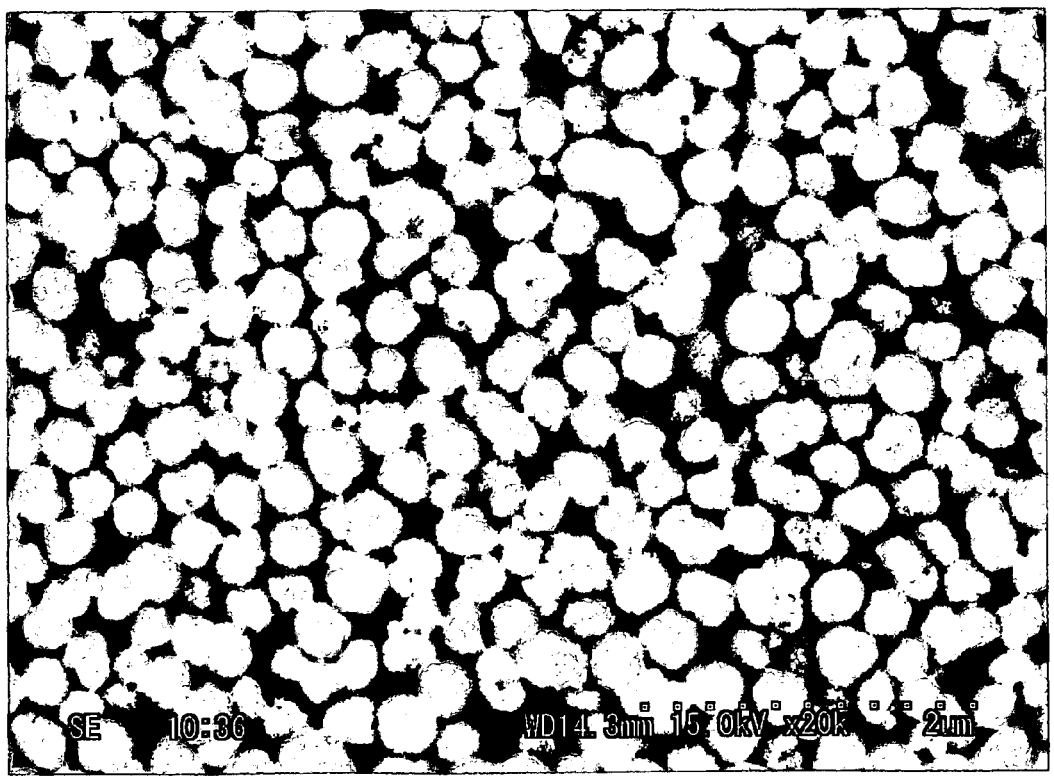
FIG. 10 is an SEM photograph of spherical particles of Example 1-W.

FIGS. 1 to 11 are SEM photographs of typical particles obtained in Examples of the present invention. Spherical particles are shown in FIGS. 1, 4, 10 and 11, disk-shaped particles are shown in FIG. 2, paired particles are shown in FIG. 3, rectangular-parallelepiped-shaped particles are shown in FIGS. 5 and 9, hexagonal-plate-shaped particles are shown in FIG. 6, rice-grain-shaped particles are shown in FIG. 7, and cylindrical particles are shown in FIG. 8.

The SEM photographs of FIGS. 1 to 11 are representative examples of particles obtained in Examples. The shapes of the particles of the present invention are observed based on the SEM photographs magnified about 10,000 times to about 20,000 times. As can be seen from FIGS. 1 to 11, the particles of the present invention have characteristics that they have a uniform shape and size and they hardly undergo agglomeration and show a monodisperse state in each photograph. Another characteristic of the particles is that the particle diameters are relatively small.

Figure 11:
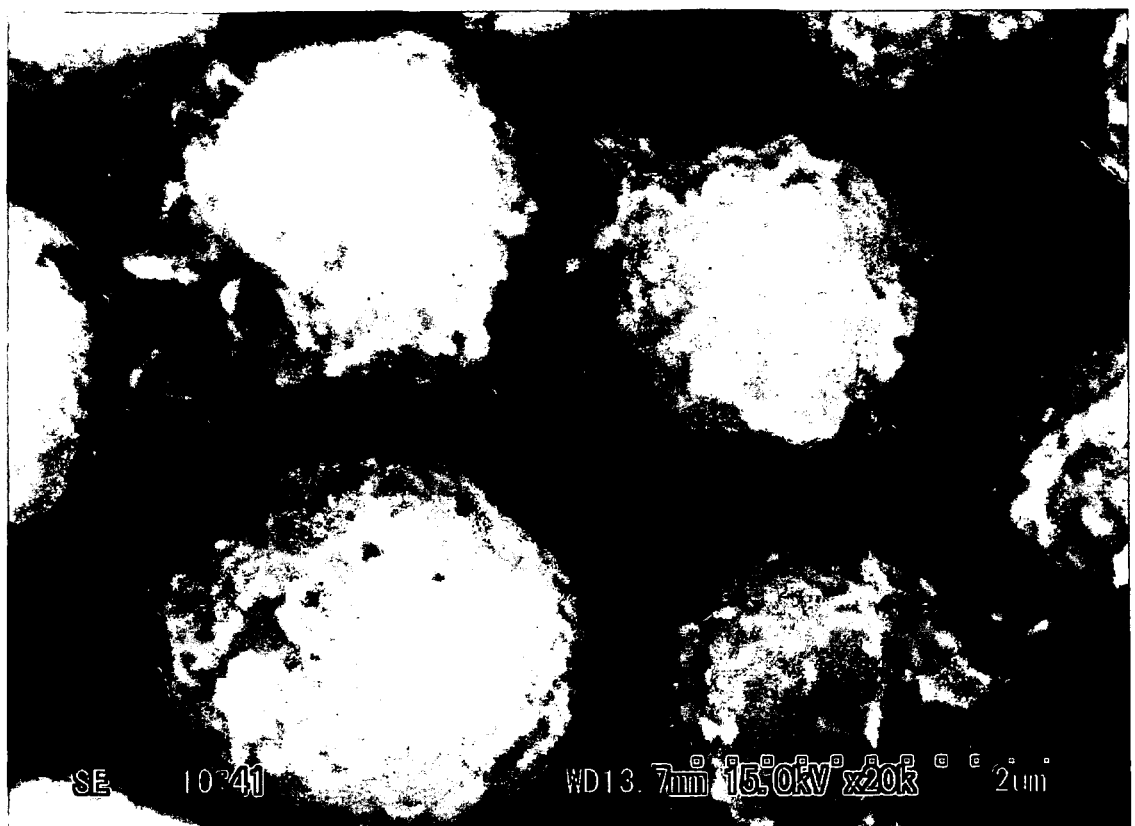
FIG. 11 is an SEM photograph of spherical particles of Example 1-N.

The shapes of the particles of the present invention will be described based on FIGS. 1 to 11. Spherical particles are shown in FIGS. 1, 4, 10 and 11, and the particles of FIGS. 1, 4 and 11 are nearly perfectly spherical particles. While the spherical particles of FIG. 4 have smooth surfaces, the spherical particles of FIGS. 1, 10 and 11 have small pits and projections or wrinkles on the surfaces thereof. Disk-shaped particles are shown in FIG. 2. The front surface and back surface of the disk-shaped particle have a nearly symmetric dome shape, and the disk-shaped particles resemble go stones. The disk-shaped particles of FIG. 2 have a smooth surface.

FIG. 3 shows paired particles. The particle is characterized in that two disk-shaped particles each of which has a flat bottom surface and a dome-shaped top surface are joined together on the bottom surfaces to form a paired shape and there is space between the bottom surfaces except for the central portions thereof. In the joined central portions, aluminum salt hydroxide which joins the two disks together exists. The paired particle apparently resembles a hamburger.

FIG. 5 shows an example of rectangular-parallelepiped-shaped particles. The particle of FIG. 5 is a rectangular parallelepiped close to a cube and has smooth surfaces. FIG. 9 shows another example of rectangular-parallelepiped-shaped particles. It may be possible to say that the particle of FIG. 9 is an octahedron-shaped particle. FIG. 6 shows hexagonal-plate-shaped particles. The hexagonal-plate-shaped particle is a plate-shaped particle having a hexagonal surface formed by six sides. The six sides do not have to have the same length, and the contact point between two sides may be rounded.

FIG. 7 shows rice-grain-shaped particles. The reflected shape of the rice-grain-shaped particle is oval, and a cross section perpendicular to the longitudinal direction has a nearly circular shape. The particles of FIG. 7 have small wrinkles on the surfaces thereof. FIG. 8 shows an example of cylindrical particles. The cylindrical particle may have a swollen middle portion like a sake barrel (or a wine barrel) or may be a hollow cylinder whose cross section is nearly circular. The particles of FIG. 8 has a number of pits and projections on the surfaces thereof.

Thus, as can be seen from the photographs of FIGS. 1 to 11, the particles of the present invention are characterized in that they show a uniform particle shape and size and good dispersibility in each photograph. The above shapes of the particles are classified and expressed for convenience sake, and small changes in the shapes and mixing of other particles in small quantity are allowed. Further, smoothness, the existence of very small pits and projections and the existence of small wrinkles on the surfaces of the particles are not particularly limited. The pits, projections and wrinkles may or may not exist.

A measure for specifying the shape of particles is Wadell's circularity and sphericity which have been used in the powder industry field.

The Wadell's sphericity s is defined by the following formula.

$s$=(surface area of sphere having equal volume to particle)/(surface area of particle)

The shape of a particle becomes closer to a perfect sphere as s becomes closer to 1. The Wadell's circularity c is defined by the following formula.

$c$=(circumferential length of circle having equal area to reflected area of particle)/(circumferential length of reflected surface of particle)

The shape of a particle becomes closer to a perfect circle as c becomes closer to 1.

The spherical particles in the present invention have ball-like shapes as shown in FIGS. 1, 4, 10 and 11, and the above Wadell's sphericity s preferably satisfies $0.95 \leq s \leq 1$.

The disk-shaped (go-stone-shaped) particles in the present invention each have a shape formed by rotating an elliptical shape around the minor axis which is an rotation axis as shown in FIG. 2. More specifically, with respect to a projection image of a particle viewed from the direction of the rotation axis, the Wadell's circularity c preferably satisfies $0.95 \leq c \leq 1$, and the (minor axis/major axis) ratio a of an elliptical cross section preferably satisfies $0.05 \leq a \leq 0.5$.

The paired particles in the present invention are particles each of which is a pair of hemispherical particles stuck together (at the flat surfaces thereof) as shown in FIG. 3. Further, there is a gap (groove) along the peripheries of the stuck surfaces of the two hemispherical particles. The minor axis/major axis ratio t of the paired particle preferably satisfies $0.1 \leq t \leq 0.5$, the (width of the gap between the stuck surfaces of the hemispheres)/minor axis ratio u preferably satisfies $0.05 \leq u \leq 0.5$.

The rectangular-parallelepiped-shaped particles in the present invention have a shape similar to a hexahedron (including a cube) or an octahedron as shown in FIGS. 5 and 9, and the above Wadell's sphericity s preferably satisfies $0.5 \leq s \leq 0.8$.

The hexagonal-plate-shaped particles in the present invention have a flat, hexagonal cylindrical shape as shown in FIG. 6. With respect to a projection image of a particle viewed from above or from below, the Wadell's circularity c preferably satisfies $0.95 \leq c \leq 0.99$, and the thickness/(length of diagonal of hexagon) ratio b preferably satisfies $0.05 \leq b \leq 0.5$.

The rice-grain-shaped particles in the present invention have a shape formed by rotating an elliptical shape around the major axis which is an rotation axis as shown in FIG. 7. The (minor axis/major axis) ratio a of an ellipse preferably satisfies $1 \leq a \leq 0.5$, and the above Wadell's sphericity s preferably satisfies $0.4 \leq s \leq 0.75$.

The cylindrical particles in the present invention have a cylindrical shape and a similar cylindrical shape in which the radius in the central portion in the height direction of the cylinder is up to 1.0 to 1.2 times larger than the radii of the top surface and the bottom surface. With respect to projection images of the top surface and the bottom surface, the Wadell's circularity c preferably satisfies $0.95 \leq c \leq 0.99$, and the value b of height/(diameter of the top surface or bottom surface) preferably satisfies $1.5 \leq b \leq 3$. Such a shape is shown in FIG. 8.

According to the present invention, as described above, the organic acid anion containing aluminum salt hydroxide particles can provide various shapes such as a sphere, a disk (go stone), a pair, a rectangular parallelepiped, a hexagonal plate, a rice grain and a cylinder according to applications and purposes, and the particle diameters of the particles can be controlled. That is, as to the shape of the particles, the organic acid anion containing aluminum salt hydroxide particles can be provided in an optimum shape according to applications and purposes. For example, the particles can be provided in a spherical shape when added as an anti-blocking agent, provided in a rectangular parallelepiped shape, disk shape (go stone shape), spherical shape or hexagonal plate shape as a filler for an epoxy sealer for a semiconductor or provided in a paired shape, cylindrical shape, rice grain shape or disk shape (go stone shape) as an adsorbent. Meanwhile, as to the particle diameter as well, the organic acid anion containing aluminum salt hydroxide particles can be provided with an optimum particle diameter according to applications and a required packing rate. In addition, to achieve the closest packing, it is also possible to use a mixture of two types of organic acid anion containing aluminum salt hydroxide particles having different average particle diameters.

The organic acid anion containing aluminum salt hydroxide particles of the present invention have an average secondary particle diameter measured by a laser diffraction method of 0.1 to 12 μm, preferably 0.1 to 10 μm. The average secondary particle diameter is more preferably 0.2 to 5 μm, particularly preferably 0.2 to 2 μm.

In a suitable embodiment, the organic acid anion containing aluminum salt hydroxide particles of the present invention show low-cohesiveness even when they have a small particle diameter of not larger than 0.5 μm, particularly not larger than 2 μm and also show excellent dispersibility when filled in a resin as compared with conventionally known aluminum salt hydroxide particles. Thus, when the particle diameter is so formed as to be ½ or smaller of the visible wavelength (0.4 to 0.7 μm) and the refractive index is set at a value close to that of a resin by optimizing the shape and composition of the particles, a resin composition having thin haze and very good transparency can be provided.

The organic acid anion containing aluminum salt hydroxide particles provided by the present invention hardly undergo secondary flocculation and retain a uniform particle diameter despite the relatively small particle diameter. As a method of evaluating particle size uniformity, a method is often used which expresses the extent of particle size distribution by the value of the ratio $D_{75}/D_{25}$ wherein $D_{25}$ represents particle diameters whose cumulative frequency is 25% and $D_{75}$ represents particle diameters whose cumulative frequency is 75% from smaller particle diameters with respect to the total number of particles, with the horizontal axis representing the particle diameters and the vertical axis representing cumulative frequency.

In the present invention, a value represented by the $D_{75}/D_{25}$ is referred to as a particle size distribution ratio ($D_R$).

The organic acid anion containing aluminum salt hydroxide particles provided in the present invention show a particle size distribution ratio ($D_R$) of 1 to 1.8 regardless of the shape of the particles and show particle size uniformity which has not been achieved in the prior art. In a preferred application embodiment, the range of the $D_R$ is 1.01 to 1.5, particularly preferably 1.02 to 1.3, most preferably 1.03 to 1.2.

As another method of evaluating particle size uniformity, it is possible to evaluate the particle size uniformity by a half width, a standard deviation, a variation coefficient and the like. These evaluation methods have correlations with one another, and any of the $D_R$, half width and standard deviation can be used as an evaluation criterion.

Further, the particle size uniformity can be expressed by the ratio of particles having particle diameters falling within a given range whose center is the average particle diameter or the median particle diameter to all particles. Depending on the shape of particle size distribution, this ratio is useful as a measure for evaluating the particle size uniformity as another parameter independent of the above $D_R$ ($D_{75}/D_{25}$), half width and standard deviation. When this measure using the average particle diameter as the center thereof is used, the proportion of particles whose particle diameters are 0.85 to 1.15 times as large as the average particle diameter measured by a laser diffraction method of the organic acid anion containing aluminum salt hydroxide particles in the present invention is 40% or higher, preferably 60% or higher, particularly preferably 80% or higher, based on all particles. That is, the proportion of particles which satisfy the following expression:

$$(\text{average particle diameter} \times 0.85) < W \, \mu m < (\text{average particle diameter} \times 1.15)$$

is 40% or higher, preferably 60% or higher, particularly preferably 70% or higher.

The higher the proportion (%) of particles having W in the above range, the higher the uniformity of the particles becomes. The higher the upper limit of the proportion, the better. In the present invention, the upper limit of the proportion is generally 95%, preferably 97%.

The organic acid anion containing aluminum salt hydroxide particles of the present invention have a specific surface area measured by a BET method of 0.1 to 300 m²/g, preferably 0.5 to 250 m²/g. These particles can be selected for a suitable range in specific surface area according to applications.

For example, when these particles are used in an application requiring an anti-blocking property, the specific surface area by the BET method is preferably 0.1 to 30 m2/g, more preferably 2 to 10 m²/g. Meanwhile, when the particles are used as an adsorbent or a carrier, the specific surface area by the BET method is preferably 0.5 to 300 m²/g, more preferably 2 to 250 m²/g.

Organic acid anion containing aluminum salt hydroxide particles having such particle size uniformity show good dispersibility as an additive to a resin or rubber. Hence, when a resin or rubber containing a conventionally known additive is compared with a resin or rubber containing the organic acid anion containing aluminum salt hydroxide particles of the present invention, the percentage of elongation of the latter is 5 to 10 times higher than that of the former in a tensile test. Thus, the particles of the present invention can provide higher flexibility. Further, conventionally known fillers such as spherical silica have a problem that even if particles with two different average particle-diameters which can satisfy filling conditions determined by the Andreasen's formula are combined and filled in a semiconductor sealing resin, the closest packing cannot be achieved in reality since the particle size distribution ratio ($D_R$) which represents particle size uniformity exceeds 1.8 and the proportion of particles which satisfy the above formula (average particle diameter×0.85)<W μm< (average particle diameter×1.15) is lower than 40%. Meanwhile, since the organic acid anion containing aluminum salt hydroxide particles of the present invention have a uniform particle diameter, the closest packing matching the theory can be achieved. The color of a resin in which the organic acid anion containing aluminum salt hydroxide particles of the present invention is milky white, and yellowing or whitening of the resin is not seen. Thus, the particles of the present invention are useful as additives to resins or rubber, particularly as a filler, an anti-blocking agent, an ultraviolet absorber and an infrared absorber.

The organic acid anion containing aluminum salt hydroxide particles of the present invention are water-insoluble, have excellent acid resistance and can maintain the basic structure thereof in a strongly acidic environment. Accordingly, the particles of the present invention are useful as a filter material or a filter aid in food processing or an additive to resins for food containers which should avoid elution of components.

The organic acid anion containing aluminum salt hydroxide particles of the present invention are also useful as an adsorbent for a malodorous gas or a deodorant. In this case, the particles of the present invention can be used alone or in admixture with fibers, a resin or the like.

The organic acid anion containing aluminum salt hydroxide particles of the present invention show good dye absorbability. Therefore, they are useful as a dye carrier, a coloration aid and an additive to color toner for an electronograph.

Next, a method for producing the organic acid anion containing aluminum salt hydroxide particles of the present invention will be described.

For example, when the inorganic acid ion represented by B in the formula (I) is a sulfate ion, the organic acid anion containing aluminum salt hydroxide particles of the present invention can be produced by adding an alkali hydroxide aqueous solution containing M in the formula (I) to a mixed solution comprising aluminum sulfate, a sulfate of M' in the formula (I), a sulfate of M in the formula (I) and an organic acid and/or an organic acid salt, e.g., oxalic acid ($H_2C_2C_4$) to cause a heating reaction. If necessary, the produced organic acid anion containing aluminum salt hydroxide particles may be separated by filtration, washed and dried to give hydrated powder of the organic acid anion containing aluminum salt hydroxide particles.

When the above reaction is carried out without adding the organic acid, the value ($D_R$) of particle size distribution ratio which represents the particle size uniformity of the organic acid anion containing aluminum salt hydroxide particles to be produced becomes large. Further, when the organic acid is not used, the shape of the particles to be produced is limited to a spherical shape or shapes based on the spherical shape. That is, the particles cannot be formed in a shape suited to an application freely, so that the object of the present invention cannot be achieved.

In the present invention, the particle size uniformity and shape of the particles are ensured by the amount of the organic acid added. Hence, unlike a conventionally known method, there is no need to monitor pH constantly and control the pH during the reaction so as to secure particle size uniformity. Further, since particles having an already uniform particle diameter and shape are obtained at the end of the reaction, there is no need to perform grinding and classification.

It is indisputable that the presence of the organic acid in the reaction significantly contributes to ensuring of the particle size uniformity of the organic acid anion containing aluminum salt hydroxide particles and determination of the shape of the particles in the present invention. However, its specific effects are still-unknown at the present time. A sulfate of M in the formula (I) acts as a catalyst.

The organic acid anion containing aluminum salt hydroxide particles of the present invention are excellent in (1) acid resistance, (2) fineness of the particles and (3) variety of the shape of the particles, as compared with so-called conventionally known alunite compound particles containing no organic acid.

Thus, the organic acid anion containing aluminum salt hydroxide particles of the present invention are excellent in dispersibility in a resin and a high filing property, as compared with the conventionally known alunite compound particles. Further, a resin composition containing the particles of the present invention are excellent in acid resistance and physical strength. Further, the particles of the present invention can be used in a variety of applications as compared with the conventionally known alunite compound particles which are limited to particular shapes.

In the present invention, under stationary reaction conditions, the particle diameter, shape and chemical and physical properties of the organic acid anion containing aluminum salt hydroxide particles to be produced are uniquely determined by a combination of the types of the above cation M and organic acid. Meanwhile, for a certain combination of cations (M in the formula (I)), the particle diameter, shape and chemical and physical properties of the organic acid anion containing aluminum salt hydroxide particles to be produced are uniquely determined by reaction conditions, that is, the molar ratio of a sulfate of M' in the formula (I) to an alkali hydroxide, the heating reaction temperature and the type of the organic acid. That is, organic acid anion containing aluminum salt hydroxide particles having a desired particle diameter, shape and chemical and physical properties can be produced by selecting a combination of Ms, the type of the organic acid and heating reaction conditions. In any case, uniformity in the particle diameter and shape of the particles is maintained due to the presence of the organic acid in the heating reaction. This will be further described later.

Further, in the above reaction, when a mixed solution comprising aluminum sulfate, a sulfate of M' and an organic acid, e.g., a mixed solution comprising aluminum sulfate, titanium sulfate and citric acid, is subjected to a heating reaction together with an alkali hydroxide mixed solution containing the cation M, a solid solution of the organic acid anion containing aluminum salt hydroxide particles which has a different composition from that of the above solid solution can be produced.

In the above reaction, when the concentration of M' is increased, a composition having hydrolysates of these ions, i.e., oxides, hydroxides, basic salts or acid salts thereof, on the surfaces of the organic acid anion containing aluminum salt hydroxide particles can be obtained. In particular, a hydrolysate of tin, titanium, copper or the like can be deposited on the surfaces of the organic acid anion containing aluminum salt hydroxide particles by selecting tin sulfate, titanium sulfate or the like as the sulfate of M'.

Such particles carrying metals on the surfaces can also be obtained by a conventionally known method which causes an organic acid anion containing aluminum salt hydroxide to carry a variety of metal compounds. For example, they can be obtained by a method comprising adding organic acid anion containing aluminum salt hydroxide particles and a base such as sodium hydroxide to a titanium sulfate solution so as to deposit a hydrolysate of titanium on the surface of the organic acid anion containing aluminum salt hydroxide.

In the present invention, when a sulfate of M' including aluminum, a mixed solution of organic acids of two or more different types and a mixed solution comprising a sulfate of the cation M are subjected to a heating reaction together with an alkali hydroxide solution containing the cation M, a solid solution of the organic acid anion containing aluminum salt hydroxide particles which has a different composition from that of the above solid solution can be produced.

In the present invention, for synthesis of the organic acid anion containing aluminum salt hydroxide particles, a nitrate, a phosphate or a silicate may be used in place of a sulfate of M which is added as a catalyst.

The present inventors have found that repeated use of $M_2SO_4$-containing reaction mother liquor produced in the reaction causes no adverse effect on the organic acid anion containing aluminum salt hydroxide particles to be produced. The method of the present invention is advantageous because repeated use of the mother liquor can keep production costs low.

In the organic acid anion containing aluminum salt hydroxide particles of the present invention, a desired particle diameter and particle shape can be obtained at the end of the heating reaction process by setting reaction conditions so as to obtain particles of a required shape and particle diameter according to various applications. Thus, a subsequent grinding process is not needed at all, thereby reducing the number of processes. This also helps keep production costs low.

Thus, according to the present invention, there is provided a method for producing organic acid anion containing aluminum salt hydroxide particles, which comprises carrying out a heating reaction in the presence of an organic acid or organic acid salt when an alkali hydroxide solution selected from the second group is added to a mixed solution comprising an inorganic salt of $Al^{3+}$ or at least one cation selected from the group consisting of $Al^{3+}$, $Cu^{2+}$, $Zn^{2+}$, $Ni^{2+}$, $Sn^{4+}$, $Zr^{4+}$, $Fe^{2+}$, $Fe^{3+}$ and $Ti^{4+}$ (the first group) and a sulfate or nitrate of at least one selected from the group consisting of $Na^+$, $K^+$, $NH_4^+$ and $H_3O^+$ (the second group) to cause the heating reaction.

In the above method, a sulfate containing at least $Al^{3+}$ is suitable as the inorganic acid salt of the cation.

The reaction temperature in the method of the present invention is preferably higher than the boiling point and not higher than 300° C., more preferably 90 to 250° C. When the reaction temperature is lower than 90° C., the reaction rate becomes very low, resulting in low production efficiency. On the other hand, when the reaction temperature is higher than 300° C., special equipment is required disadvantageously.

The reaction may be carried out under sealed conditions using an autoclave or the like or under open conditions. The reaction temperature preferably ranges from 100° C. to 200° C., particularly preferably from 120° C. to 170° C.

The concentration of the aluminum salt in the reaction of the present invention is preferably 0.01 to 3.0 mol/L, more preferably 0.01 to 2 mol/L. When the concentration of the aluminum salt is lower than 0.01 mol/L, productivity is low, while when it is higher than 3 mol/L, interparticle agglomeration is liable to occur, and uniformity in the size and particle diameter of the particles becomes difficult to be controlled.

The concentration of the organic acid in the reaction solution in the present invention is preferably equal to or lower than a half of the concentration (mol) of the aluminum salt, more preferably ½₀ to ½ of the concentration of the aluminum salt. When the value of (concentration of organic acid)/(concentration of aluminum salt) is higher than ½ or lower than ½₀, the shape, size and particle diameter of the particles become non-uniform. In the present invention, an organic carboxylic acid or an organic oxycarboxylic acid is preferred as the organic acid. An organic carboxylic acid and an organic oxycarboxylic acid which have 1 to 15 carbon atoms, preferably 2 to 10 carbon atoms, are suitable, and an organic carboxylic acid and an organic oxycarboxylic acid which have 1 to 4 carboxyl groups, preferably 1 or 2 carboxyl groups, in a molecule are particularly desirable. These organic acids may be in the form of a salt or an isomer. A specific example of the organic acid is at least one selected from the group consisting of oxalic acid, citric acid, malic acid, tartaric acid, glyceric acid, gallic acid and lactic acid, isomers thereof and salts thereof.

The molar ratio of the sulfate of M' to the alkali hydroxide MOH in the reaction according to the method of the present invention is 1:3.8 to 4.7. The reaction formula wherein the molar ratio is 1:4 is shown above. When the value of the alkali hydroxide is less than 4, the reaction may not proceed to a satisfactory extent. Meanwhile, when the value of the alkali hydroxide is higher than 4.4, boehmite may be produced. In consideration of these points, the molar ratio is more preferably 1:4 to 4.4.

The organic acid anion containing aluminum salt hydroxide particles in the present invention is an additive showing excellent dispersibility even when used as it is. However, their dispersibility in a resin, rubber or the like can be further improved by surface-treating the particles with at least one surface treating agent selected from the group consisting of a higher fatty acid, an anionic surfactant, a phosphoric ester, a coupling agent, a polyhydric alcohol and a fatty acid ester.

Illustrative examples of surface treating agents which are preferably used include higher fatty acids having 10 or more carbon atoms such as stearic acid, erucic acid, palmitic acid, lauric acid and behenic acid, and alkali metal salts of these higher fatty acids; sulfates of higher alcohols such as stearyl alcohol and oleyl alcohol; anionic surfactants such as a sulfate, amide bond sulfate, ester bond sulfate, ester bond sulfonate, amide bond sulfonate, ether bond sulfonate, ether bond alkylaryl sulfonate, ester bond alkylaryl sulfonate and amide bond alkylaryl sulfonate of a polyethylene glycol ether; phosphoric esters such as acid and alkali metal salts and amine salts of a mixture comprising orthophosphoric acid and a monoester and/or diester of oleyl alcohol, stearyl alcohol or the like; silane coupling agents such as γ-(2-aminoethyl)aminopropyl trimethoxysilane, γ-(2-aminoethyl)aminopropylmethyl dimethoxysilane, N-β-(N-vinylbenzylaminoethyl)-γ-aminopropyl Trimethoxysilane.hydrochloride, γ-glycidoxypropyl trimethoxysilane, γ-mercaptopropyl trimethoxysilane, methyl trimethoxysilane, methyl triethoxysilane, vinyl triacetoxysilane, γ-chloropropylmethyl trimethoxysilane, hexamethyldisilazane, γ-anilinopropyl trimethoxysilane, vinyl trimethoxysilane, octadecyl dimethyl [3-(trimethoxysilyl)]ammonium chloride, γ-chloropropylmethyl dimethoxysilane, γ-mercaptopropylmethyl dimethoxysilane, methyl trichlorosilane, dimethyl dichlorosilane, trimethyl chlorosilane, vinyl trichlorosilane, vinyl triethoxysilane, vinyl tris(β-methoxyethoxy)silane, β-(3,4-epoxycyclohexyl)ethyl trimethoxysilane, γ-glycidoxypropylmethyl ethoxysilane, γ-glycidoxypropyl triethoxysilane, γ-methacryloxypropylmethyl dimethoxysilane, γ-methacryloxypropylmethyl diethoxysilane, γ-methacryloxypropylmethyl triethoxysilane, N-β(aminoethyl)γ-aminopropylmethyl dimethoxysilane, N-β(aminoethyl)γ-aminopropyl trimethoxysilane, N-β(aminoethyl)γ-aminopropyl triethoxysilane, γ-aminopropyl trimethoxysilane, γ-aminopropyl triethoxysilane, N-phenyl-γ-aminopropyl trimethoxysilane, γ-glycidoxypropyl trimethoxysilane and γ-methacryloxypropyl trimethoxysilane; titanate-based coupling agents such as isopropyl triisostearoyl titanate, isopropyl tris(dioctyl pyrophosphate)titanate, isopropyl tri(N-aminoethyl-aminoethyl) titanate, isopropyl tridecyl benzenesulfonyl titanate, tetraoctyl bis(ditridecyl phosphate)titanate, bis(dioctyl pyrophosphate)oxyacetate titanate, isopropyl tridecyl benzenesulfonyl titanate, tetraisopropyl bis(dioctyl phosphite)titanate, tetra(2,2-diallyoxymethyl-1-butyl)bis-(ditridecyl) phosphite titanate, bis(dioctyl pyrophosphate)ethylene titanate, isopropyl trioctanoyl titanate, isopropyl dimethacryl isostearoyl titanate, isopropyl isostearoyl diacryl titanate, isopropyl tri(dioctyl phosphate)titanate, isopropyl tricumyl phenyl titanate, dicumyl phenyl oxyacetate titanate and diisostearoyl ethylene titanate; aluminum-based coupling agents such as acetalkoxy aluminum diisopropylate; and polyhydric alcohols and fatty acids such as triphenyl phosphite, diphenyl.tridecyl phosphite, phenyl.ditridecyl phosphite, tri.nonylphenyl phosphite, 4,4'-butylidene-bis(3-methyl-6-t-butylphenyl)-ditridecyl phosphite, trilauryl thiophosphite, glycerine monostearate and glycerine monooleate.

As a method of surface-treating the organic acid anion containing aluminum salt hydroxide particles with the above surface treating agents, a method known per se can be used. For example, the surface treatment can be carried out in the following manner.

When an alkali hydroxide solution is added to a mixed solution comprising a sulfate of a trivalent metal, a sulfate and/or nitrate of a monovalent cation and an organic acid to cause a heating reaction so as to produce organic acid anion containing aluminum salt hydroxide particles and the produced organic acid anion containing aluminum salt hydroxide particles are separated by filtration, washed and dried, the surface treating agent may be added after any of the heating reaction step, filtration step, washing step and drying step. When the organic acid anion containing aluminum salt hydroxide particles are kneaded into rubber, a resin or the like, the surface treating agent may be added at that time. The surface treatment can be carried out by a conventionally known method such as a wet method or a dry method.

The surface treating agent is added in an amount of 0.01 to 10 parts by weight, preferably 0.05 to 5 parts by weight, based on 100 parts by weight of the organic acid anion containing aluminum salt hydroxide particles.

The organic acid anion containing aluminum salt hydroxide particles in the present invention may be surface-modified by use of the following inorganic oxides, metals and ceramics to impart flowability and electric conductivity to the organic acid anion containing aluminum salt hydroxide particles. The above inorganic oxides, metals and ceramics include silica, alumina, antimony oxide, tin oxide, manganese dioxide, zirconium oxide, zinc oxide, titanium oxide, antimony doped tin oxide, tin doped indium oxide, ytterbium oxide and tungsten trioxide.

Further, the organic acid anion containing aluminum salt hydroxide particles in the present invention may be surface-modified by use of the following inorganic oxides, metals and ceramics to impart flowability and thermal conductivity to the organic acid anion containing aluminum salt hydroxide particles. The above inorganic oxides, metals and ceramics include aluminum oxide, zinc oxide, barium oxide, magnesium oxide, calcium oxide, basic magnesium carbonate, hydrotalcite, charcoal alumite compounds, inorganic silicates, diamond, copper, silicon carbide, aluminum, aluminum nitride, iron, beryllia, titanium nitride and chromium nitride.

The organic acid anion containing aluminum salt hydroxide particles surface-modified by the above materials may be kneaded into a resin or coated on another substrate material such as various alloys, ceramics or carbons by a method such as CVD, plasma CVD or PVD according to applications to impart given functions to the resin or substrate material.

When the organic acid anion containing aluminum salt hydroxide particles in the present invention are surface-modified with an alkali metal silicate, mica, zeolite, imogolite or the like, the surface-modified particles can be used as various adsorbents such as a moisture adsorbent and a moisture controller, a volatile organic compound (VOC) remover or a carrier for a dye or the like.

Further, when the organic acid anion containing aluminum salt hydroxide particles in the present invention are surface-modified with an ultraviolet absorber such as titanium oxide, the surface-modified particles are very useful as a heat insulating agent for a film for agriculture, ultraviolet/infrared absorbers for cosmetics and an ultraviolet degradation inhibitor for rubber.

Surface modification of the organic acid anion containing aluminum salt hydroxide particles with the above inorganic oxide or the like can be carried out by use of a conventionally known method such as a method comprising performing polishing and burning while a polyhydric alcohol is added to a mixture of the organic acid anion containing aluminum salt hydroxide particles and, for example, titanium oxide powder.

The surface modifying agent is added in an amount of 0.01 to 100 parts by weight, preferably 0.05 to 50 parts by weight, based on 100 parts by weight of the organic acid anion containing aluminum salt hydroxide particles.

The organic acid anion containing aluminum salt hydroxide particles of the present invention can be used after burned at a temperature suitable for an application within a range of 300 to 1,000° C. for 2 hours.

The organic acid anion containing aluminum salt hydroxide particles of the present invention can be added to organic a polymer compound described below either directly or after subjected to the above surface treatment, surface modification, burning or the like.

The organic polymer compounds include resins such as resole type and novolak type phenol resins, a melamine resin, a melamine-urea cocondensation resin, a melamine-benzoguanamine cocondensation resin, a melamine-phenol resin, a bisphenol A type epoxy resin, a brominated epoxy resin, a bisphenol F type epoxy resin, a novolak type epoxy resin, an alicyclic epoxy resin, a glycidyl amine type epoxy resin, a glycidyl ester type epoxy resin, a heterocyclic epoxy resin, an urea resin, an urea-formaldehyde-furfuryl alcohol based resin, an unsaturated polyester resin, a silicone resin, a polyurethane, vinyl chloride, a vinyl chloride-ethylene copolymer, a vinyl chloride-vinyl acetate copolymer, a vinylidene chloride copolymer, a polyethylene, a polyethylene imine, a polyethylene glycol, a polyethylene terephthalate, a poly(ethylene-chlorotrifluoroethylene), an acrylic resin, a polyethylene naphthalate, a polybutylene terephthalate, a polymicrooxylenedimethylene terephthalate, an aliphatic polyketone, a polystyrene, an ABS resin, a polypropylene, a polyamide 6, a polyamide 6-6, a polyamide 6T, a polyamide MXD 6, a polyacetal, a polyester, a polycarbonate, a modified polyphenylene ether, a polysulfone, a polyarylate, a polyetherimide, a polyethersulfone, a polyamide imide, a polyphenylene sulfide and a liquid crystal polyester, and alloys of resins selected from the above resins; synthetic rubber such as chloroprene rubber, styrene butadiene rubber, butyl rubber, ethylene propylene rubber, nitrile rubber, chlorosulfonated polyethylene rubber, urethane rubber, silicone rubber, fluorine rubber, polyisoprene rubber and butadiene rubber; synthetic fibers such as nylon, vinylon, acryl fibers and rayon; natural organic polymers such as cellulose, alginic acid, starch, proteins, collagen and natural resins (such as shellac, dammar, amber, copal and rosin); and semisynthetic polymers such as cellulose based resins (such as cellulose acetate, cellulose nitrate and cellulose acetate butyrate), casein plastic and soy protein plastic.

A combination of the synthetic polymer and the organic acid anion containing aluminum salt hydroxide particles can be said to be a particularly suitable combination because the particles can be added to the polymer in high density and the resulting composition completely retains mechanical and optical properties and other properties inherent to the pre-addition synthetic polymer.

The organic acid anion containing aluminum salt hydroxide particles of the present invention are preferably added to the above organic polymer compound as an additive in an amount of 0.5 to 90 parts by weight based on 100 parts by weight of the organic polymer compound. When the amount is smaller than 0.5 parts, the effect as an additive is not satisfactory, while when the amount is larger than 90 parts, the-effect is not improved. Therefore, the amount is more preferably 1 to 80 parts. Meanwhile, the amount thereof as a filler is preferably 0.5 to 100 parts by weight. When the amount is smaller than 0.5 parts, the effect as a filler is not satisfactory, while when it is larger than 100 parts, the effect is not significantly improved.

The organic acid anion containing aluminum salt hydroxide particles of the present invention have thin haze in the visible light region. Hence, when they are added to the following inorganic compounds, the refractive index and dispersion can be controlled.

The above inorganic compounds include soda glass, lead crystal glass, borosilicate glass, glass ceramic, aluminosilicate glass, potash glass, quartz and various oxide and nonoxide ceramics.

The organic acid anion containing aluminum salt hydroxide particles of the present invention can be added to the above inorganic compound by a method known per se, e.g., burning a mixture of the above inorganic compound and the organic acid anion containing aluminum salt hydroxide particles.

The organic acid anion containing aluminum salt hydroxide particles of the present invention can be advantageously used in a wide variety of fields such as an additive and a hardening accelerator for cement; an additive for foods and a filter aid for fermented foods such as beer and soy sauce; an additive and a carrier for agricultural chemicals and an additive for various agricultural films; an additive for a semiconductor sealer and an additive for heat-resistant ceramics; toner for an electronograph, a toner additive, a cleaning agent, and a carrier for two-component toner; an additive and various carriers for drugs; an additive for cosmetics, a deodorant, an antimicrobial agent, an antifungal agent, an antialgous agent, and carriers therefore; a carrier and an additive for dyes and pigments; catalysts; a deodorant for fibers, a colorant for rubber and resins, an anchor coating agent, a thermal conductive material carrier, a magnetic material carrier, an electric conductivity imparting material carrier, an electromagnetic wave absorber carrier, an anti-blocking agent and other additives; an additive for glass and a foaming agent for recycling of waste glass; a polishing agent, standard particles for correction of instrument, a spacer for a liquid crystal panel, ultraviolet and infrared absorbers, a deodorant, an agent for treating radioactive wastes, and adsorbents for environmental pollutants and volatile organic compounds (VOC).

The first effect of the present invention is to be able to provide a method for producing organic acid anion containing aluminum salt hydroxide particles having an optimum shape and particle diameter suited for an application at low cost, with good reproducibility and in high yield.

The second effect of the present invention is to be able to provide organic acid anion containing aluminum salt hydroxide particles which are fine particles, have a uniform particle shape and particle diameter, show high dispersibility and low moisture absorbability and have acid resistance.

The third effect of the present invention is to be able to provide an additive and a filler for resins, rubbers and the like which show good dispersibility and can impart an anti-blocking property, acid resistance and other properties to a resin, a rubber or the like without degrading physical properties such as transparency and tensile strength even when added to the resin, the rubber or the like.

The fourth effect of the present invention is to be able to provide particles and carriers whose physical properties, particularly an adsorbing ability and a carrying ability, do not deteriorate even in an environment in which relative humidity is high and in a strongly acidic environment.

EXAMPLES

Hereinafter, the present invention will be further described with reference to examples. However, the present invention shall not be limited by these examples. Further, all chemicals used below are first class grade chemicals of Wako Pure Chemical Industries, Ltd. unless otherwise stated.

Example 1-A

Figure 12:
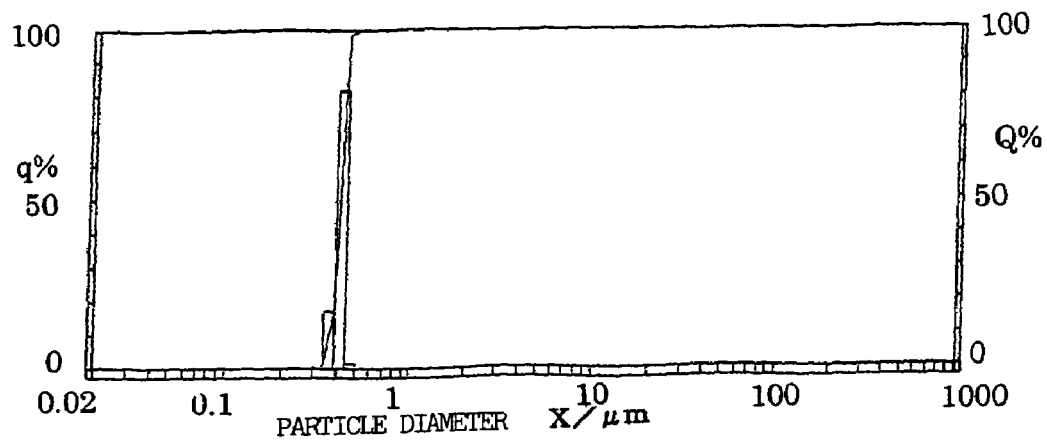
FIG. 12 is a particle size distribution diagram of the organic acid anion containing aluminum salt hydroxide particles of Example 1-A, wherein the horizontal axis represents particle diameters, the vertical axis on the left side represents frequency (%: proportion to total number, indicated by bars), and the vertical axis on the right side represents cumulative frequency (proportion to total number, indicated by line).

Synthesis of $(NH_4)_{0.92}Al_3(SO_4)_{1.95}(C_2C_4)_{0.099}(OH)_{5.82} \cdot 0.3H_2O$ 0.2 mol of aluminum sulfate and 0.2 mol of ammonium sulfate were dissolved in 600 ml of pure water, and 0.025 mol of oxalic acid was added. Under agitation, 89 ml of 25% ammonium hydroxide solution was added to the mixture, and the resulting solution was heated at 100° C. for 1 hour. After cooling, the reaction mixture was filtered and the precipitate was rinsed with water, and dried at 95° C. for 15 hours. As a result, organic acid anion containing aluminum salt hydroxide particles which showed spherical shapes shown in the SEM photograph of FIG. 1 were obtained. The average particle diameter and BET specific surface area of the obtained organic acid anion containing aluminum salt hydroxide particles are shown in Table 1-1, and the particle size distribution thereof is shown in FIG. 12.

Example 1-B

Figure 13:
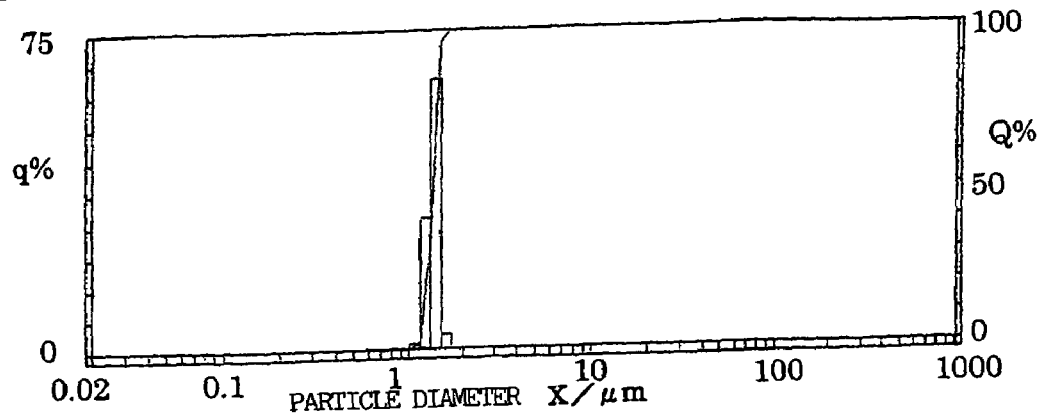
FIG. 13 is a particle size distribution diagram of the organic acid anion containing aluminum salt hydroxide particles of Example 1-B.

Synthesis of $Na_{1.02}Al_3(SO_4)_{2.03}(C_2O_4)_{0.06}(OH)_{5.84} \cdot 0.2H_2O$ 0.2 mol of aluminum sulfate and 0.2 mol of sodium sulfate were dissolved in 600 ml of pure water, and 0.015 mol of oxalic acid was added. Under agitation, 0.8 mol of sodium hydroxide was added to the mixture which was then subjected to a hydrothermal treatment at 170° C. for 8 hours. After cooling, the reaction mixture was filtered and the precipitate was rinsed with water, and dried at 95° C. for 15 hours. As a result, organic acid anion containing aluminum salt hydroxide particles showing disk shapes shown in the SEM photograph of FIG. 2 were obtained. The properties of the obtained organic acid anion containing aluminum salt hydroxide particles are shown in Table 1-1, and the particle size distribution of the particles is shown in FIG. 13.

Example 1-C

Figure 14:
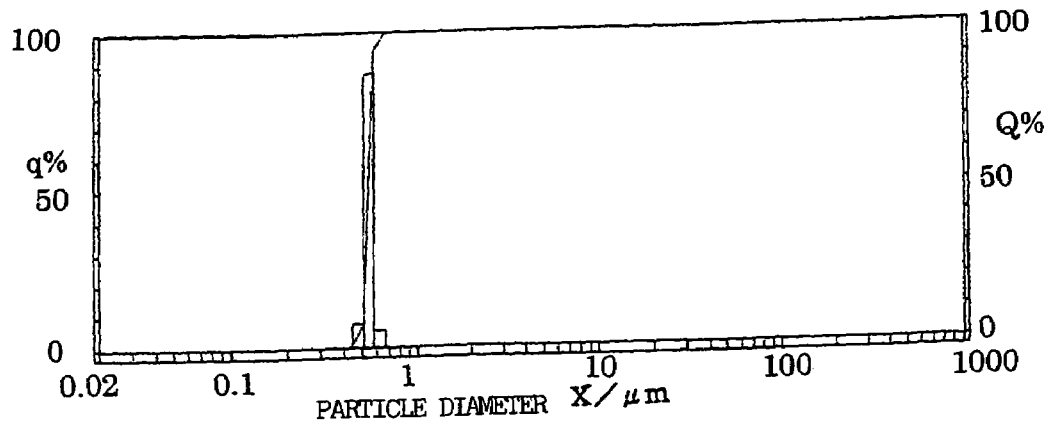
FIG. 14 is a particle size distribution diagram of the organic acid anion containing aluminum salt hydroxide particles of Example 1-C.

Synthesis of $Na_{1.06}Al_3(SO_4)_{2.04}(C_2O_4)_{0.096}(OH)_{5.79} \cdot 0.2H_2O$ 0.025 mol of oxalic acid was added to a mixture of 194 ml of 1.03 mol/L aluminum sulfate solution and 400 ml of 0.5 mol/L sodium sulfate solution. Under agitation, 240 ml (0.81 mol) of sodium hydroxide solution was further added, and the resulting solution was then subjected to a hydrothermal treatment at 180° C. for 15 hours. Other treatment conditions are the same as those used in Example 1-A. The properties of the obtained organic acid anion containing aluminum salt hydroxide particles are shown in Table 1-1, and the particle size distribution thereof is shown in FIG. 14. The particles were in the shape of pairs as shown in the SEM photograph of FIG. 3.

Example 1-D

Figure 15:
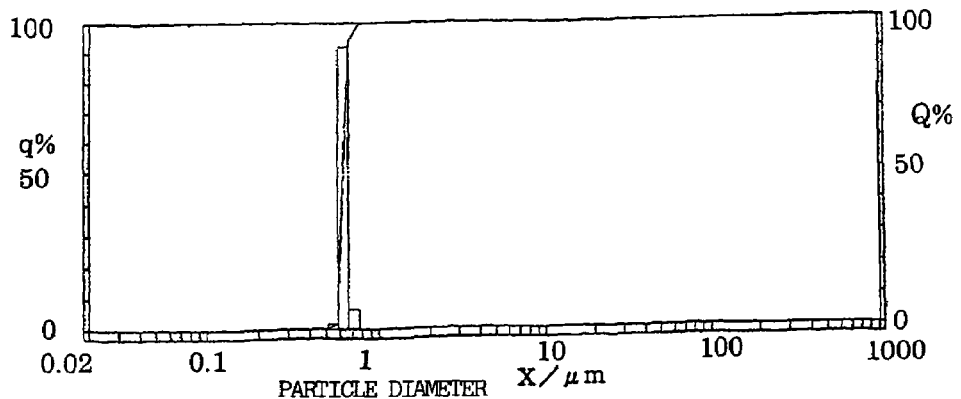
FIG. 15 is a particle size distribution diagram of the organic acid anion containing aluminum salt hydroxide particles of Example 1-D.

Synthesis of $K_{0.98}Al_3(SO_4)_{1.99}(C_2O_4)_{0.089}(OH)_{5.82} \cdot 0.1H_2O$ 0.1 mol of aluminum sulfate solution was dissolved in 500 ml of water, 0.1 mol of potassium nitrate and 0.0125 mol of oxalic acid were added, the mixture was agitated at room temperature for 30 minutes, 200 ml (0.4 mol) of potassium hydroxide solution was further added, and the mixture was subjected to a hydrothermal treatment at 170° C. for 10 hours. Other treatment conditions are the same as those used in Example 1-A. The properties of the obtained organic acid anion containing aluminum salt hydroxide particles are shown in Table 1-1, and the particle size distribution thereof is shown in FIG. 15. The particles were in the shape of spheres as shown in the SEM photograph of FIG. 4.

Example 1-E

Synthesis of $(H_3O)Al_3(SO_4)_{2.01}(C_2O_4)_{0.09}(OH)_{5.8} \cdot 0.1H_2O$ 0.1 mol of aluminum sulfate was dissolved in 500 ml of water. This solution was mixed with 208 ml (0.125 mol) of aluminum hydroxide suspension, and 0.05 mol of oxalic acid was added. After fully agitated, the mixture was subjected to a hydrothermal treatment at 170° C. for 5 hours. Other treatment conditions are the same as those used in Example 1-A. The properties of the obtained organic acid anion containing aluminum salt hydroxide particles are shown in Table 1-1. The particles were in the shape of rectangular parallelepiped as shown in the SEM photograph of FIG. 5.

Example 1-F

Synthesis of $Na_{0.93}Al_3(SO_4)_{2.01}(C_2O_4)_{0.092}(OH)_{5.73} \cdot 0.2H_2O$ 0.2 mol of aluminum sulfate and 0.2 mol of sodium sulfate were dissolved in 600 ml of water, and 0.025 mol of oxalic acid was added. Under agitation, 180 ml (0.9 mol) of sodium hydroxide aqueous solution was added to the mixture. The mixture was then agitated at room temperature for 30 minutes and then subjected to a hydrothermal treatment at 180° C. for 20 hours. After cooling, the reaction mixture was filtered and the precipitate was rinsed with water, and dried at 95° C. for 15 hours to obtain organic acid anion containing aluminum salt hydroxide particles. The properties of the organic acid anion containing aluminum salt hydroxide particles are shown in Table 1-1. The particles were in the shape of hexagonal plates as shown in the SEM photograph of FIG. 6.

Example 1-G

Synthesis of $Na_{1.11}Al_{2.98}(SO_4)_{1.96}(C_2O_4)_{0.201}(OH)_{5.73} \cdot 0.8H_2O$ 0.2 mol of aluminum sulfate and 0.2 mol of sodium sulfate were dissolved in 600 ml of pure water, and 0.05 mol (6.3 g) of oxalic acid was added. Further, under agitation, 0.8 mol of sodium hydroxide was added to the mixture which was then subjected to a hydrothermal treatment at 170° C. for 2 hours. After cooling, the reaction mixture was filtered and the precipitate was rinsed with water, and dried at 105° C. for 15 hours to obtain organic acid anion containing aluminum salt hydroxide particles having disk shapes. The properties of the obtained organic acid anion containing aluminum salt hydroxide particles are shown in Table 1-1.

Example 1-H

Synthesis of $[Na_{0.9}K_{0.01}]Al_3(SO_4)_{1.83}(C_2O_4)_{0.13}(OH)_{6.07} \cdot 0.6H_2O$ At room temperature, 1,420.4 g of sodium sulfate, 10 g of potassium sulfate, 315.15 g of oxalic acid, and 9.8 L (10 mol) of aluminum sulfate solution were mixed and dissolved, and ion-exchange water was added to the mixture to adjust the amount of the mixture to 27 L. This mixed solution and 12 L (41 mol) of sodium hydroxide solution were added to a 2.5-L reaction tank and agitated. The reaction solution was transferred to a 50-L reaction tank, and ion-exchange water was added to adjust the amount of the reaction solution to 40 L. After the reaction solution was further agitated at room temperature for 10 hours, it was subjected to a hydrothermal treatment at 170° C. for 2 hours. After the hydrothermal treatment, the reaction mixture was filtered and the precipitate was rinsed with water and dried at 105° C. for 15 hours to obtain organic acid anion containing aluminum salt hydroxide particles. The properties of the obtained disk-shaped organic acid anion containing aluminum salt hydroxide particles are shown in Table 1-1.

Example 1-I

Synthesis of $Na_{1.11}Al_3(SO_4)_{1.86}(C_6H_5O_7)_{0.14}(OH)_{5.97} \cdot 0.8H_2O$ At room temperature, ion-exchange water was added to 99.43 g of sodium sulfate, 36.96 g of citric acid ($H_3C_6H_5O_7 \cdot H_2O$) and 660 ml (0.7 mol) of aluminum sulfate solution to adjust the amount of the mixture to 1.7 L, and they were dissolved by agitation subsequently. While this mixed solution was agitated, 853 ml (2.87 mol) of sodium hydroxide solution was added, and the resulting solution was agitated at room temperature for another 10 hours and then subjected to a hydrothermal treatment at 170° C. for 2 hours. After the hydrothermal treatment, the reaction mixture was filtered and the precipitate was rinsed with water and dried at 105° C. for 15 hours to obtain organic acid anion containing aluminum salt hydroxide particles. The properties of the obtained spherical organic acid anion containing aluminum salt hydroxide particles are shown in Table 1-1.

Example 1-J

Synthesis of $Na_{0.99}Al_3(SO_4)_{1.92}(C_4H_4O_6)_{0.27}(OH)_{5.34} \cdot 0.5H_2O$ At room temperature, ion-exchange water was added to 99.43 g of sodium sulfate, 26.27 g of tartaric acid ($H_2C_4H_4O_6$) and 660 ml (0.7 mol) of aluminum sulfate solution to adjust the amount of the mixture to 1.7 L, and they were dissolved by agitation at room temperature subsequently. 853 ml (2.87 mol) of sodium hydroxide solution was added to this mixed solution, and the mixture was agitated for 10 hours and then subjected to a hydrothermal treatment at 170° C. for 2 hours. After the hydrothermal treatment, the reaction mixture was filtered and the precipitate was rinsed with water and dried at 105° C. for 15 hours. The properties of the obtained organic acid anion containing aluminum salt hydroxide particles are shown in Table 1-1. The particles were in the shape of rice grains as shown in the SEM photograph of FIG. 7.

Example 1-K

Synthesis of $Na_{1.02}Al_3(SO_4)_{1.92}(C_4H_4O_5)_{0.12}(OH)_{5.94} \cdot 0.6H_2O$ Spherical organic acid anion containing aluminum salt hydroxide particles were obtained in the same manner as in Example 1-I except that DL-malic acid was used in place of citric acid. The properties of the organic acid anion containing aluminum salt hydroxide particles are shown in Table 1-1.

Example 1-L

Synthesis of $K_{0.99}Al_3(SO_4)_{1.99}(C_6H_5O_7)_{0.14}(OH)_{5.59} \cdot 0.5H_2O$ Spherical organic acid anion containing aluminum salt hydroxide particles were obtained in the same manner as in Example 1-I except that potassium sulfate was used in place of sodium sulfate as a catalyst, citric acid was used in place of oxalic acid and potassium hydroxide was used in place of sodium hydroxide. The properties of the organic acid anion containing aluminum salt hydroxide particles are shown in Table 1-1.

Example 1-M

Synthesis of $Na_{0.95}Al_3(SO_4)_{1.87}(C_2O_4)_{0.05}(C_4H_4O_5)_{0.07}(OH)_{5.90} \cdot 0.6H_2O$ Spherical organic acid anion containing aluminum salt hydroxide particles were obtained in the same manner as in Example 1-I except that two organic acids, i.e., 0.026 mol of oxalic acid and 0.026 mol of tartaric acid, were used in place of citric acid. The properties of the organic acid anion containing aluminum salt hydroxide particles are shown in Table 1-1.

Example 1-N

Synthesis of $Na_{1.02}Al_3(SO_4)_{1.98}[C_6H_2(OH)_3COO]_{0.12}(OH)_{5.94} \cdot 0.8H_2O$ Spherical organic acid anion containing aluminum salt hydroxide particles were obtained in the same manner as in Example 1-I except that gallic acid [$C_6H_4(OH)_3COOH$] was used in place of citric acid. The properties of the organic acid anion containing aluminum salt hydroxide particles are shown in Table 1-1. The particles were in the shape of spheres as shown in the SEM photograph of FIG. 11.

Example 1-O

Synthesis of $Na_{0.98}Al_3(SO_4)_{1.97}[HOCH_2CH(OH)COO]0.20(OH)_{5.84} \cdot 0.6H_2O$ Organic acid anion containing aluminum salt hydroxide particles were obtained in the same manner as in Example 1-I except that DL-glyceric acid [$HOCH_2CH(OH)COOH$] was used in place of citric acid. The properties of the organic acid anion containing aluminum salt hydroxide particles are shown in Table 1-1. The particles were in the shape of cylinders as shown in the SEM photograph of FIG. 8.

Example 1-P

Synthesis of $Na_{1.03}Al_3(SO_4)_{1.99}[CH_3CH(OH)COO]_{0.22}(OH)_{5.83} \cdot 0.7H_2O$ Organic acid anion containing-aluminum salt hydroxide particles were obtained in the same manner as in Example 1-I except that L-lactic acid [$CH_3CH(OH)COOH$] was used in place of citric acid. The properties of the organic acid anion containing aluminum salt hydroxide particles are shown in Table 1-1. The particles were in the shape of round rectangular parallelepiped as shown in the SEM photograph of FIG. 9.

Example 1-Q

Synthesis of $[(H_3O)Na_{0.03}]Al_3(SO_4)_{1.99}(C_2O_4)_{0.04}(OH)_{5.97} \cdot 0.6H_2O$ While 192 ml (0.2 mol) of aluminum sulfate solution was agitated, 3.15 g of oxalic acid was added. Further, 15.6 g of aluminum hydroxide was also added to prepare precipitate slurry. Ion-exchange water was added to the slurry to dilute it to 850 ml. After agitated at room temperature for 1 hour, the resulting solution was subjected to a hydrothermal treatment at 170° C. for 5 hours by means of an autoclave. The treated mixture was filtered and the precipitate was rinsed with water, dried and ground to obtain spherical organic acid anion containing aluminum salt hydroxide particles. The properties of the obtained particles are shown in Table 1-1.

Example 1-R

Synthesis of $[NH_4Na_{0.02}]Al_3(SO_4)_{2.02}(C_2O_4)_{0.14}$
$(OH)_{5.70}\cdot 0.5H_2O$ After 264.28 g of ammonium sulfate, 5.0 g of sodium sulfate, 63.03 g of oxalic acid and 1.9 L (2 mol) of aluminum sulfate solution were mixed together, ion-exchange water was added to adjust the amount of the mixture to 8.0 L, and the resulting mixture was agitated. After all of them were dissolved at 45° C., 1.9 L (17.25 mol) of ammonia solution was added to the solution. After agitated for another 1 hour, the mixture was subjected to a hydrothermal treatment at 100° C. for 1 hour. After the hydrothermal treatment, the reaction mixture was filtered and the precipitate was rinsed with water and dried (at 105° C. for 15 hours) to obtain organic acid anion containing aluminum salt hydroxide particles. The properties of the obtained particles are shown in Table 1-1.

Example 1-S

Synthesis of $Na_{1.01}[Al_{2.63}Zn_{0.37}](SO_4)_{2.10}(C_2O_4)_{0.13}$
$(OH)_{5.18}\cdot 0.6H_2O$ 194 ml (0.2 mol) of aluminum sulfate solution, 28.4 g (0.2 mol) of sodium sulfate and 6.3 g (0.05 mol) of oxalic acid were mixed together, ion-exchange water was added to dilute the mixture to 600 ml, and crystals were dissolved under agitation. 14.38 g (0.05 mol) of zinc sulfate was added to this solution and dissolved. Further, 235 ml (0.8 mol) of sodium hydroxide solution was added to the mixed solution at room temperature in 6 minutes. After agitated at room temperature for 1 hour, the solution was subjected to a hydrothermal treatment at 170° C. for 2 hours. After the hydrothermal treatment, the reaction mixture was filtered and the precipitate was rinsed with water and dried (at 105° C. for 15 hours) to obtain spherical organic acid anion containing aluminum salt hydroxide particles. The properties of the obtained particles are shown in Table 1-1.

Example 1-T

Synthesis of $Na_{1.01}[Al_{2.86}Ni_{0.14}](SO_4)_{2.02}(C_2O_4)_{0.20}$
$(OH)_{5.43}\cdot 1.2H_2O$ Organic acid anion containing aluminum salt hydroxide particles were obtained in the same manner as in Example 1-S except that 7.35 g (0.03 mol) of nickel sulfate was used in place of zinc sulfate. The properties of the obtained disk-shaped particles are shown in Table 1-1.

Example 1-U

Synthesis of $Na_{0.96}[Al_{2.76}Fe_{0.13}Zn_{0.11}](SO_4)_{2.01}$
$(C_2O_4)_{0.19}(OH)_{5.32}\cdot 0.60H_2O$ Organic acid anion containing aluminum salt hydroxide particles were obtained in the same manner as in Example 1-S except that 0.02 mol ($FeSO_4\cdot 7H_2O$: 5.6 g) of iron sulfate and 0.02 mol ($ZnSO_4\cdot 7H_2O$: 5.8 g) of zinc sulfate were used in place of zinc sulfate. The properties of the obtained disk-shaped particles are shown in Table 1-2.

Figure 16:
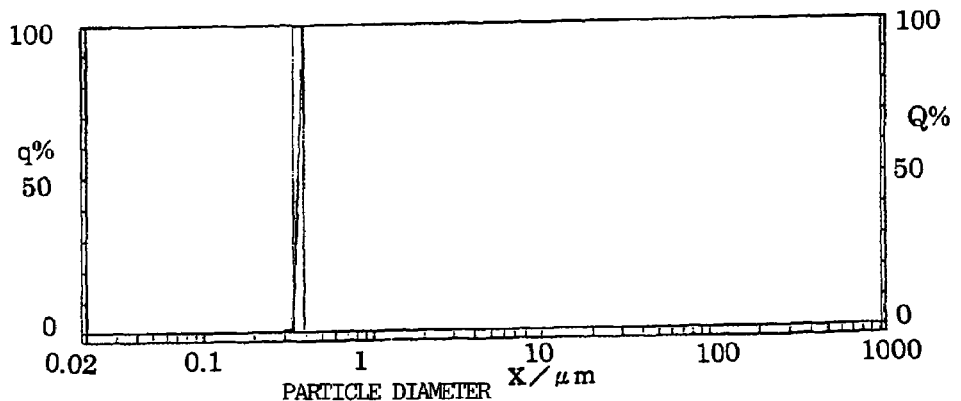
FIG. 16 is a particle size distribution diagram of the organic acid anion containing aluminum salt hydroxide particles of Example 1-V.

Example 1-V $Na_{1.12}Al_3[(PO_4)_{1.71}(SO_4)_{0.29}](C_2O_4)_{0.12}$
$(OH)_{4.17}\cdot 0.90OH_2O$ 194 ml (0.2 mol) of aluminum sulfate, 28.4 g (0.2 mol) of sodium sulfate and 6.3 g of oxalic acid were mixed together, ion-exchange water was added to dilute the mixture to 500 ml, and crystals were dissolved under agitation. 400 ml of solution containing 0.2 mol (8.4 g, purity: 95%) of sodium hydroxide and 0.7 mol (266.1 g) of $Na_3PO_4\cdot 12H_2O$ was added to this solution in 6 minutes. After agitated for 1 hour, the solution was subjected to a hydrothermal treatment at 170° C. for 2 hours. After the hydrothermal treatment, the reaction mixture was filtered and the precipitate was rinsed with water and dried (at 105° C. for 15 hours) to obtain rectangular-parallelepiped-shaped organic acid anion containing aluminum salt hydroxide particles. The properties of the obtained particles are shown in Table 1-2. The particle size distribution of the particles is shown in FIG. 16.

Example 1-W $K_{1.02}Al_3[(SO_4)_{1.79}(NO_3)_{0.21}](C_2O_4)_{0.11}$
$(OH)_{6.01}\cdot 0.85H_2O$ 194 ml (0.2 mol) of aluminum sulfate, 20.3 g (0.2 mol) of potassium nitrate and 5.1 g of oxalic acid were mixed together, ion-exchange water was added to dilute the mixture to 500 ml, and crystals were dissolved under agitation. 400 ml of solution containing 0.8 mol (52.81 g, purity: 85%) of potassium hydroxide was added to this solution in 10 minutes. After agitated for 2 hours, the solution was subjected to a hydrothermal treatment at 150° C. for 2 hours. After the hydrothermal treatment, the reaction mixture was filtered and the precipitate was rinsed with water and dried (at 105° C. for 15 hours) to obtain organic acid anion containing aluminum salt hydroxide particles. The properties of the obtained particles are shown in Table 1-2. The particles were in the shape of spheres as shown in the SEM photograph of FIG. 10.

Comparative Example 1

$Na_{0.96}Al_3(SO_4)_{2.01}(OH)_{5.94}\cdot 0.63H_2O$

Ion-exchange water was added to 127 ml of 1.025 mol/L aluminum sulfate and 18.46 g (0.13 mol) of sodium sulfate to adjust the amount of the mixture to 500 ml. While the mixture was agitated at room temperature, 154 ml of 3.382N sodium hydroxide solution was added in about 1 minute. After agitated for another 20 minute, the mixture was transferred to an autoclave to undergo a hydrothermal reaction at 170° C. for 2 hours. After cooled to 25° C., the reaction mixture was filtered and the precipitate was rinsed with 500 ml of water and dried at 105° C. for 22 hours, thereby obtaining spherical alunite type compound particles containing no organic acid anions. The properties of the obtained alunite type compound particles are shown in Table 1-2.

Example 2

Synthesis of Carrier Composition

Example 2-A

Synthesis of Titanium Hydrolysate Carrier Composition

Organic acid anion containing aluminum salt hydroxide particles containing titanium and a titanium hydrolysate were obtained by using 0.08 mol of titanium sulfate (64 g of 30% solution) in place of zinc sulfate in Example 1-R. The properties of the obtained titanium hydrolysate carrier composition are shown in Table 2. The particles were in the shape of disks.

Example 2-B

Synthesis of Copper Hydrolysate Carrier Composition

Copper and copper hydrolysate organic acid anion containing aluminum salt hydroxide particles were obtained by using 0.03 mol ($CuSO_4 \cdot 5H_2O$: 7.49 g) of copper sulfate in place of zinc sulfate in Example 1-R. The properties of the obtained copper hydrolysate carrier composition are shown in Table 2. The particles were in the shape of pairs.

Example 2-C

Synthesis of Zirconium Hydrolysate Carrier Composition

Organic acid anion containing aluminum salt hydroxide particles containing zirconium and a zirconium hydrolysate were obtained by using 0.03 mol of zirconium oxychloride ($ZrCl_2O \cdot 8H_2O$: 9.67 g) in place of zinc sulfate in Example 1-R. The properties of the obtained zirconium hydrolysate carrier composition are shown in Table 2. The particles were in the shape of rectangular parallelepiped.

Example 3

Measurement of Particle Size Distribution Width

The particle sizes of the organic acid anion containing aluminum salt hydroxide particles synthesized in Examples 1-A to 2-C were measured by a laser diffraction method. In the obtained particle size distribution, when particle diameters at 25% and 75% values of cumulative particle size distribution curve were represented by $D_{25}$ and $D_{75}$ and the value of $D_{75}/D_{25}$ was calculated, the ratio showed a value of 1 to 1.2. In addition, the proportion e (%) of particles having an average particle diameter of A μm and a particle diameter W μm which satisfies $0.85A < W < 1.15A$ was read from each particle size distribution. The results are shown in Tables 1-1 and 1-2.

TABLE 1-1

| Example | Sulfate | Alkali | Sulfate or Nitrate | Organic Acid or Organic Acid Salt |
|---|---|---|---|---|
| 1-A | $Al_2(SO_4)_3$ | $NH_4OH$ | $(NH_4)_2SO_4$ | Oxalic Acid |
| 1-B | $Al_2(SO_4)_3$ | NaOH | $Na_2SO_4$ | Oxalic Acid |
| 1-C | $Al_2(SO_4)_3$ | NaOH | $Na_2SO_4$ | Oxalic Acid |
| 1-D | $Al_2(SO_4)_3$ | KOH | $KNO_3$ | Oxalic Acid |
| 1-E | $Al_2(SO_4)_3$ | NaOH | — | Oxalic Acid |
| 1-F | $Al_2(SO_4)_3$ | NaOH | $Na_2SO_4$ | Oxalic Acid |
| 1-G | $Al_2(SO_4)_3$ | NaOH | $Na_2SO_4$ | Oxalic Acid |
| 1-H | $Al_2(SO_4)_3$ | NaOH | $Na_2SO_4, K_2SO_4$ | Oxalic Acid |
| 1-I | $Al_2(SO_4)_3$ | NaOH | $Na_2SO_4$ | Citric Acid |
| 1-J | $Al_2(SO_4)_3$ | NaOH | $Na_2SO_4$ | Tartaric Acid |
| 1-K | $Al_2(SO_4)_3$ | NaOH | $Na_2SO_4$ | DL-malic Acid |
| 1-L | $Al_2(SO_4)_3$ | KOH | $K_2SO_4$ | Citric Acid |
| 1-M | $Al_2(SO_4)_3$ | NaOH | $Na_2SO_4$ | Oxalic Acid, Tartaric Acid |
| 1-N | $Al_2(SO_4)_3$ | NaOH | $Na_2SO_4$ | Gallic Acid |
| 1-O | $Al_2(SO_4)_3$ | NaOH | $Na_2SO_4$ | DL-glyceric Acid |
| 1-P | $Al_2(SO_4)_3$ | NaOH | $Na_2SO_4$ | L-lactic Acid |
| 1-Q | $Al_2(SO_4)_3$ | NaOH | $Al(OH)_3$ | Oxalic Acid |
| 1-R | $Al_2(SO_4)_3$ | NaOH | $(NH_4)_2SO_4$ | Oxalic Acid |
| 1-S | $Al_2(SO_4)_3, ZnSo_4$ | NaOH | $Na_2SO_4$ | Oxalic Acid |
| 1-T | $Al_2(SO_4)_3, NiSo_4$ | NaOH | $Na_2SO_4$ | Oxalic Acid |

| Example | e % | Average Particle Diameter (μm) | $D_{75}/D_{25}$ | BET ($m^2/g$) | Shapes of Particles | Composition Formula |
|---|---|---|---|---|---|---|
| 1-A | 87< | 0.55 | 1.133 | 10.5 | Sphere | $(NH_4)_{0.92}Al_3(SO_4)_{1.95}(C_2O_4)_{0.099}(OH)_{5.82} \cdot 0.3H_2O$ |
| 1-B | 81.6< | 0.40 | 1.086 | 163.8 | Disk | $Na_{1.02}Al_3(SO_4)_{2.03}(C_2O_4)_{0.06}(OH)_{5.84} \cdot 0.2H_2O$ |
| 1-C | 63.6< | 1.36 | 1.132 | 2.9 | Pair | $Na_{1.06}Al_3(SO_4)_{2.04}(C_2O_4)_{0.096}(OH)_{5.79} \cdot 0.2H_2O$ |
| 1-D | 92< | 0.63 | 1.076 | 12 | Sphere | $K_{0.98}Al_3(SO_4)_{1.99}(C_2O_4)_{0.089}(OH)_{5.82} \cdot 0.1H_2O$ |
| 1-E | — | 2.44 | 1.121 | 4.1 | Rectangular parallelepiped | $(H_3O)Al_3(SO_4)_{2.01}(C_2O_4)_{0.09}(OH)_{5.8} \cdot 0.1H_2O$ |

TABLE 1-1-continued

| | e % | Avg Particle Diameter (μm) | $D_{75}/D_{25}$ | BET (m²/g) | Shapes | Composition Formula |
|---|---|---|---|---|---|---|
| 1-F | — | 0.61 | 1.147 | 10.5 | Hexagonal Plate | $Na_{0.93}Al_3(SO_4)_{2.01}(C_2O_4)_{0.092}(OH)_{5.73} \cdot 0.2H_2O$ |
| 1-G | — | 0.45 | 1.072 | 154 | Disk | $Na_{1.11}Al_{2.98}(SO_4)_{1.96}(C_2O_4)_{0.201}(OH)_{5.73} \cdot 0.8H_2O$ |
| 1-H | — | 0.32 | 1.077 | 8.5 | Disk | $[Na_{0.98}K_{0.01}]Al_3(SO_4)_{1.83}(C_2O_4)_{0.13}(OH)_{6.07} \cdot 0.6H_2O$ |
| 1-I | — | 0.27 | 1.180 | 17.7 | Sphere | $Na_{1.11}Al_3(SO_4)_{1.86}(C_6H_5O_7)_{0.14}(OH)_{5.97} \cdot 0.8H_2O$ |
| 1-J | — | 0.61 | 1.189 | 89.2 | Rice Grain | $Na_{0.99}Al_3(SO_4)_{1.92}(C_4H_4O_6)_{0.27}(OH)_{5.34} \cdot 0.5H_2O$ |
| 1-K | — | 0.55 | 1.073 | 115 | Sphere | $Na_{1.02}Al_3(SO_4)1._{92}(C_4H_4O_5)_{0.12}(OH)_{5.94} \cdot 0.6H_2O$ |
| 1-L | — | 0.61 | 1.146 | 30 | Sphere | $K_{0.99}Al_3(SO_4)_{1.99}(C_6H_5O_7)_{0.14}(OH)_{5.59} \cdot 0.5H_2O$ |
| 1-M | — | 0.61 | 1.095 | 11 | Sphere | $Na_{0.95}Al_3(SO_4)_{1.87}(C_2O_4)_{0.05}(C_4H_4O_5)_{0.07}(OH)_{5.90} \cdot 0.6H_2O$ |
| 1-N | — | 0.48 | 1.142 | 35 | Sphere | $Na_{1.02}Al_3(SO_4)_{1.98}[C_6H_2(OH)_3COO]_{0.12}(OH)_{5.94} \cdot 0.8H_2O$ |
| 1-O | — | 3.05 | 1.178 | 9 | Cylinder | $Na_{0.98}Al_3(SO_4)_{1.97}[HOCH_2CH(OH)COO]_{0.20}(OH)_{5.84} \cdot 0.6H_2O$ |
| 1-P | — | 0.59 | 1.055 | 30 | Rectangular parallelepiped | $Na_{1.03}Al_3(SO_4)_{1.99}[CH_3CH(OH)COO]_{0.22}(OH)_{5.83} \cdot 0.7H_2O$ |
| 1-Q | — | 0.59 | 1.069 | 26 | Sphere | $[(H_3O)Na_{0.03}]Al_3(SO_4)_{1.99}(C_2O_4)_{0.04}(OH)_{5.97} \cdot 0.6H_2O$ |
| 1-R | — | 0.70 | 1.113 | 21 | Sphere | $[NH_4Na_{0.02}]Al_3(SO_4)_{2.02}(C_2O_4)_{0.14}(OH)_{5.70} \cdot 0.5H_2O$ |
| 1-S | — | 0.38 | 1.172 | 64 | Sphere | $Na_{1.01}[Al_{2.63}Zn_{0.37}](SO_4)_{2.10}(C_2O_4)_{0.13}(OH)_{5.18} \cdot 0.6H_2O$ |
| 1-T | — | 0.40 | 1.19 | 163.8 | Disk | $Na_{1.01}[Al_{2.86}Ni_{0.14}](SO_4)_{2.02}(C_2O_4)_{0.20}(OH)_{5.43} \cdot 1.2H_2O$ |

TABLE 1-2

| Example | Sulfate | Alkali | Sulfate or Nitrate | Organic Acid or Organic Acid Salt |
|---|---|---|---|---|
| 1-U | $Al_2(SO_4)_3$, $FeSO_4$, $ZnSO_4$ | NaOH | $Na_2SO_4$ | Oxalic Acid |
| 1-V | $Al_2(SO_4)_3$ | $Na_3PO_4$ | $Na_2SO_4$ | Oxalic Acid |
| 1-W | $Al_2(SO_4)_3$ | KOH | $KNO_3$ | Oxalic Acid |
| C. Ex. 1 | $Al_2(SO_4)_3$ | NaOH | $Na_2SO_4$ | None |

| | | Shapes of Particles | | | | |
|---|---|---|---|---|---|---|
| Example | e % | Average Particle Diameter (μm) | $D_{75}/D_{25}$ | BET (m²/g) | Shapes | Composition Formula |
| 1-U | — | 0.78 | 1.145 | 6.3 | Disk | $Na_{0.96}[Al_{2.76}Fe_{0.13}Zn_{0.11}](SO_4)_{2.01}(C_2O_4)_{0.19}(OH)_{5.32} \cdot 0.60H_2O$ |
| 1-V | — | 0.36 | 1.111 | 36.2 | Rectangular parallelepiped | $Na_{1.12}Al_3[(PO_4)_{1.71}(SO_4)_{0.29}](C_2O_4)_{0.12}(OH)_{4.17} \cdot 0.90H_2O$ |
| 1-W | — | 0.41 | 1.131 | 25.0 | Sphere | $K_{1.02}Al_3[(SO_4)_{1.79}(NO_3)_{0.21}](C_2O_4)_{0.11}(OH)_{6.01} \cdot 0.85H_2O$ |
| C. Ex. 1 | — | 2.64 | 2.16 | 9.9 | Sphere | $Na_{0.96}Al_3(SO_4)_{2.01}(OH)_{5.94} \cdot 0.63H_2O$ |

C. Ex.: Comparative Example

TABLE 2

| Example | Sulfate | Alkali | Sulfate or Nitrate | Organic Acid or Organic Acid Salt |
|---|---|---|---|---|
| 2-A | $Al_2(SO_4)_3$ | NaOH | $Na_2SO_4$ | Oxalic Acid |
| 2-B | $Al_2(SO_4)_3$ | NaOH | $Na_2SO_4$ | Oxalic Acid |
| 2-C | $Al_2(SO_4)_3$ | NaOH | $Na_2SO_4$ | Oxalic Acid |

| | | Shapes of Particles | | | | |
|---|---|---|---|---|---|---|
| Example | e % | Average Particle Diameter (μm) | $D_{75}/D_{25}$ | BET (m²/g) | Shapes | Composition Formula of Base Material |
| 2-A | — | 0.55 | 1.133 | 10.5 | Disk | $Na_{0.8938}Al_{2.533}Ti_{0.467}(SO_4)_{1.728}(C_2O_4)_{0.193}(OH)_{6.432} \cdot 0.93H_2O$ |
| 2-B | — | 1.36 | 1.132 | 2.9 | Pair | $Na_{0.99}Al_{2.83}Cu_{0.17}(SO_4)_{2.01}(C_2O_4)_{0.201}(OH)_{5.40} \cdot 1.6H_2O$ |
| 2-C | — | 0.75 | 1.100 | 6.2 | Rectangular parallelepiped | $Na_{0.987}Al_{2.89}Zr_{0.11}(SO_4)_{1.98}(C_2O_4)_{0.189}(OH)_{5.76} \cdot 0.48H_2O$ |

Example 4

Acid Resistance Test

Example 4-A (i) Sample

Example 4-A: The organic acid anion containing aluminum salt hydroxide particles synthesized in Example 1-G were used.

Comparative Example 2: The alunite type compound particles synthesized in Comparative Example 1 were used.

(ii) Test Method 1.0 g of sample was added to 100 ml of 5N $HNO_3$ aqueous solution. After agitated, the mixture was left to stand for 3 hours and then filtered by cellulose-acetate (0.2 μm). The concentrations of aluminum and $SO_4$ in the solution were determined by an atomic absorption method.

(iii) Results

Figure 17:
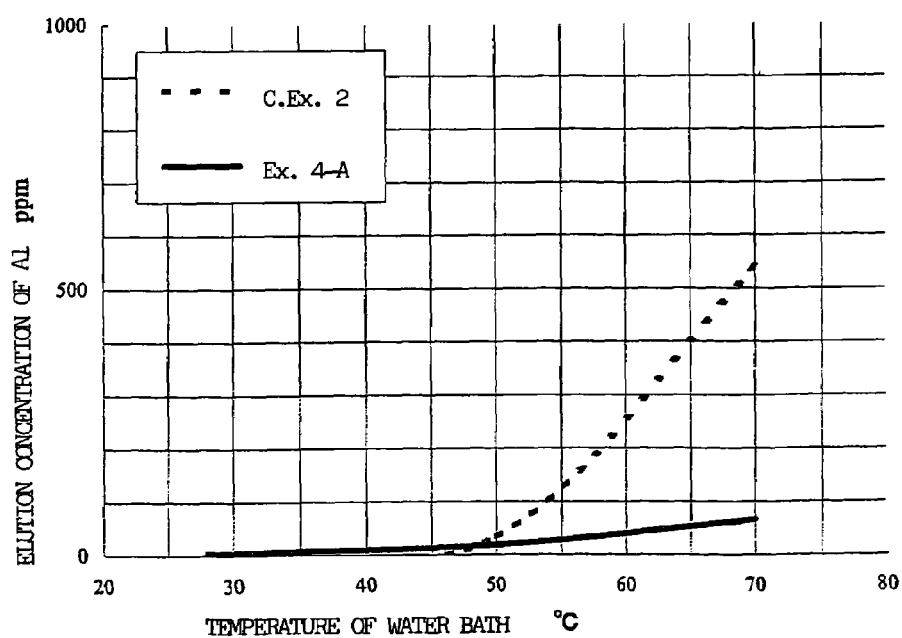
FIG. 17 is a graph illustrating the relationship between the temperature of a nitric acid solution and the concentration of Al eluted from the organic acid anion containing aluminum salt hydroxide particles of Example 4-A when immersed in the nitric acid solution.
Figure 18:
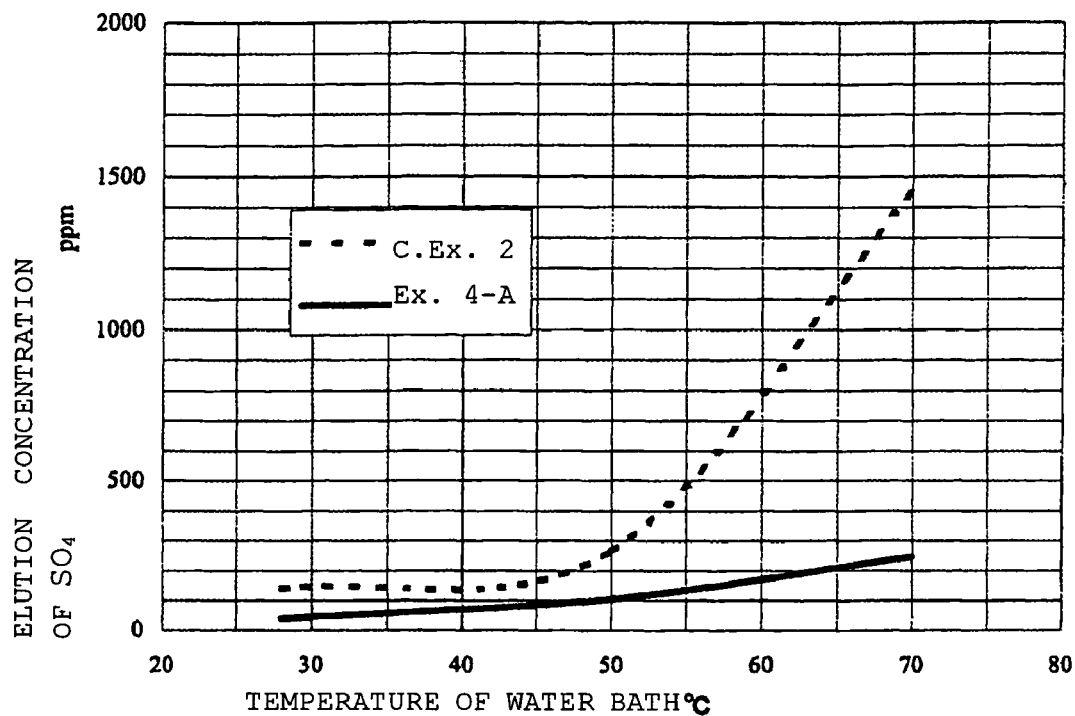
FIG. 18 is a graph illustrating the relationship between the temperature of a nitric acid solution and the concentration of $SO_4$ eluted from the organic acid anion containing aluminum salt hydroxide particles of Example 4-A when immersed in the nitric acid solution.

The results of measuring the concentrations of aluminum and $SO_4$ in the solution are shown in FIGS. 17 and 18, respectively. According to these results, it is understood that in the case of the alunite type compound particles containing no organic acid, the concentrations of aluminum and $SO_4$ in the solution increased to a great extent as the temperature of the water bath was increased, while in the case of the organic acid anion containing aluminum salt hydroxide particles of the present invention, the amounts of eluted aluminum and $SO_4$ were very small. That is, the organic acid anion containing aluminum salt hydroxide particles of the present invention were basically unchanged in an acidic environment.

This result demonstrates that the organic acid anion containing aluminum salt hydroxide particles of the present invention have greater acid resistance than the conventional alunite type compound particles because the particles of the present invention contain an organic acid.

Example 4-B (i) Preparation of Sample 500 ml of 0.4 mol/L $Al_2(SO_4)_3$ aqueous solution and a solution prepared by dissolving 17.0 g of $NaNO_3$ in 150 ml of pure water were mixed together, and oxalic acid ($H_2C_2O_4$) was added to the mixture under agitation. Further, 200 ml of 4.0 mol/L sodium hydroxide solution was added to the mixed solution which was then heated at 100° C. for 2 hours. Thereafter, the mixed solution was subjected to an autoclave treatment at 180° C. for 20 hours. After the treatment, the reaction mixture was filtered and the precipitate was rinsed with water, and dried at 95° C. for 15 hours so as to synthesize disk-shaped organic acid anion containing aluminum salt hydroxide particles.

(ii) Test Method 1.0 g of sample was mixed into HCl solutions of two different concentrations. After agitated, the mixed solutions were left to stand at room temperature for 3 hours and then filtered by cellulose-acetate (0.2 μm). The concentration of aluminum in the solutions was analyzed by an atomic absorption method.

(iii) Results

As shown in the following Table 3, as the concentration of hydrochloric acid was increased, the solubility of the sample also increased, but the degree of elution was low and the shapes of the particles were not changed.

Example 4-C (i) Preparation of Sample

A solution prepared by dissolving 61.2 g of 0.1 mol $Al_2(SO_4).15H_2O$ in 500 ml of pure water and a solution prepared by dissolving 10.2 g of $KNO_3$ in 50 ml of pure water were mixed together, and 3.15 g of oxalic acid ($H_2C_2O_4$) was added directly under agitation. Then, 200 ml of 2.36 mol/L potassium hydroxide (KOH) solution was added, and the resulting mixed solution was heat-treated at 170° C. for 20 hours. The heat-treated mixture was filtered and the precipitate was rinsed with water, and dried at 95° C. for 20 hours to obtain spherical organic acid anion containing aluminum salt hydroxide particles.

(ii) Test Method

The test was conducted in the same manner as in Example 4-B.

(iii) Result

As shown in the following Table 3, as the concentration of hydrochloric acid was increased, the solubility of the sample also increased, but the degree of elution was low and the shapes of the particles were not changed.

Example 4-D (i) Preparation of Sample 3.15 g of oxalic acid ($H_2C_2O_4$) was added to 500 ml of 0.2 mol/L $Al_2(SO_4)_3$ solution, and an aqueous solution prepared by dissolving 11.7 g of aluminum hydroxide $Al(OH)_3$ in 200 ml of pure water was added under agitation. After heated at 100° C. for at least 2 hours, the mixed solution was subjected to an autoclave treatment at 170° C. for 10 hours. The heat-treated mixture was filtered and the precipitate was rinsed with water, and dried at 95° C. for 15 hours to obtain rectangular-parallelepiped-shaped organic acid anion containing aluminum salt hydroxide particles.

(ii) Test Method

The test was conducted in the same manner as in Example 4-B.

(iii) Result

As shown in the following Table 3, as the concentration of hydrochloric acid was increased, the solubility of the sample also increased, but the degree of elution was low and the shapes of the particles were not changed.

Example 4-D

The results of making the above measurement on the sample synthesized in Example 1-G are shown in Table 3.

Example 4-E

The results of making the above measurement on the sample synthesized in Example 1-H are shown in Table 3.

Example 4-F

The results of making the above measurement on the sample synthesized in Example 1-I are shown in Table 3.

Example 4-G

The results of making the above measurement on the sample synthesized in Example 1-J are shown in Table 3.

Example 4-H

The results of making the above measurement on the sample synthesized in Example 1-K are shown in Table 3.

Example 4-I

The results of making the above measurement on the sample synthesized in Example 1-L are shown in Table 3.

Example 4-J

The results of making the above measurement on the sample synthesized in Example 1-P are shown in Table 3.

Example 4-K

The results of making the above measurement on the sample synthesized in Example 1-Q are shown in Table 3.

Results

As shown in the following Table 3, as the concentration of hydrochloric acid was increased, the solubility of the samples also increased, but the degree of elution was low and the shapes of the particles were not changed. This demonstrates that the organic acid anion containing aluminum salt hydroxide particles of the present invention have good acid resistance.

TABLE 3

| Example | Concentration of Al in HCl Solution (ppm) | |
|---|---|---|
| | 0.5 mol/L HCl | 1.0 mol/L HCl |
| 4-A | 2.0 | 3.2 |
| 4-B | 1.6 | 2.1 |
| 4-C | 29.7 | 65.7 |
| 4-D | 1.6 | 2.0 |
| 4-E | 2.1 | 3.2 |
| 4-F | 1.4 | 1.9 |
| 4-G | 1.1 | 1.5 |
| 4-H | 1.6 | 1.9 |
| 4-I | 1.2 | 1.8 |
| 4-J | 0.6 | 0.9 |
| 4-K | 8.5 | 13.6 |

Example 4-L (i) Preparation of Sample

The sample synthesized in Example 1-B was used.

(ii) Test Method 1.0 g of sample was added per 100 ml of sulfuric acid solution. After agitated, the mixture was left to stand at 27° C. for 1 hour and then filtered by cellulose-acetate (0.2 μm). The concentration of aluminum in the solution was analyzed by an atomic absorption method.

(iii) Result

Figure 19:
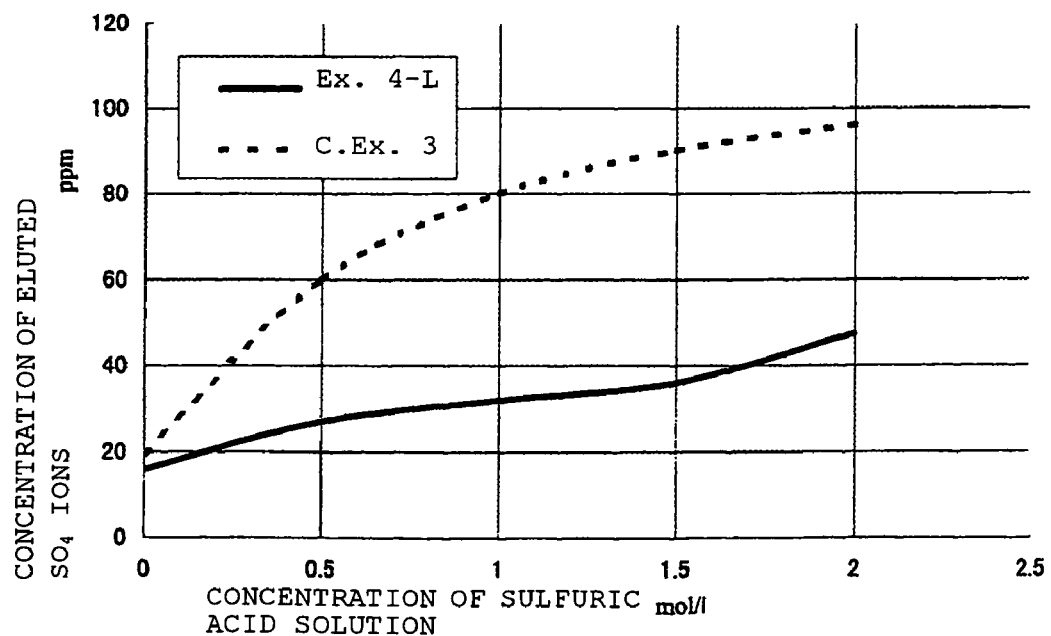
FIG. 19 is a graph illustrating the relationship between the temperature of a nitric acid solution and the concentration of $SO_4$ eluted from the organic acid anion containing aluminum salt hydroxide particles of Example 4-L when immersed in the nitric acid solution.

The concentration of $SO_4$ ions when the concentration of sulfuric acid was changed is shown in FIG. 19. As the concentration of sulfuric acid was increased, the solubility of the sample also increased but the degree of elution was low and the shape of the particles were not changed. This demonstrates that the organic acid anion containing aluminum salt hydroxide particles of the present invention have much better acid resistance than the conventional alunite type compound supposed to have good acid resistance by containing organic acid anions.

Example 5

Adsorption Test of Malodorous Gas

An adsorption test of malodorous gas was conducted, in accordance with a method which will be described later, on 12 different kinds of samples including organic acid anion containing aluminum salt hydroxide particles which were newly synthesized by the following method. As Comparative Example 4, activated carbon (product of Wako Pure Chemical Industries, Ltd.) was used.

Example 5-A

Preparation of Sample

To 500 ml of 0.4 mol/L aluminum sulfate $Al_2(SO_4)_3$ aqueous solution, 200 ml of 1 mol/L sodium sulfate $Na_2SO_4$ solution was added, 6.3 g of oxalic acid ($H_2C_2O_4$) was then added directly, and 200 ml of 93% NaOH solution was added under agitation. After heated at 100° C. for at least 10 hours, this solution was subjected to an autoclave treatment at 170° C. for 10 hours. The heat-treated mixture was filtered and the precipitate was rinsed with water, and dried at 95° C. for 15 hours to obtain disk-shaped organic acid anion containing aluminum salt hydroxide particles having a BET specific surface area of 40 $m^2/g$.

Test Method

The adsorption test was conducted in accordance with the method to be described later. The results of conducting the adsorption test are shown in Table 4.

Example 5-B

Disk-shaped organic acid anion containing aluminum salt hydroxide particles having a BET specific surface area of 97 $m^2/g$ were synthesized in the same manner as in Example 5-A except that the reaction mixture was filtered and the precipitate was rinsed with water and dried without being subjected to the autoclave treatment. The results of conducting the adsorption test are shown in Table 4.

Example 5-C

The results of conducting the adsorption test on the sample synthesized in Example 1-G are shown in Table 4.

Example 5-D

The results of conducting the adsorption test on the sample synthesized in Example 1-H are shown in Table 4.

Example 5-E

The results of conducting the adsorption test on the sample synthesized in Example 1-I are shown in Table 4.

Example 5-F

The results of conducting the adsorption test on the sample synthesized in Example 1-J are shown in Table 4.

Example 5-G

The results of conducting the adsorption test on the sample synthesized in Example 1-K are shown in Table 4.

Example 5-H

The results of conducting the adsorption test on the sample synthesized in Example 1-L are shown in Table 4.

Example 5-I

The results of conducting the adsorption test on the sample synthesized in Example 1-M are shown in Table 4.

Example 5-J

The results of conducting the adsorption test on the sample synthesized in Example 1-P are shown in Table 4.

Example 5-K

The results of conducting the adsorption test on the sample synthesized in Example 1-Q are shown in Table 4.

Comparative Example 4

The results of conducting the adsorption test on activated carbon are shown in Table 4.

Results

The following Table 4 demonstrates that the organic acid anion containing aluminum salt hydroxide particles of the present invention adsorb an alkaline substance such as ammonia easily.

TABLE 4

| Example | BET Specific Surface Area ($m^2/g$) | Malodorous Gas Adsorption Rate | | |
|---|---|---|---|---|
| | | Iso-valeric Acid | Ammonia | Trimethylamine |
| 5-A | 40 | 19 | 82 | 19 |
| 5-B | 97 | 50 | 91 | 33 |
| 5-C | 8.5 | 93 | 32 | 83 |
| 5-D | 17.7 | 25 | 82 | 85 |
| 5-E | 89.2 | 28 | 99 | 42 |
| 5-F | 115 | 31 | 96 | 43 |
| 5-G | 30 | 31 | 88 | 24 |
| 5-H | 11 | 26 | 83 | 44 |
| 5-I | 35 | 34 | 83 | 41 |
| 5-J | 9 | 18 | 75 | 22 |
| 5-K | 30 | 51 | 79 | 36 |
| C. Ex. 4 | — | 93 | 32 | 83 |

C. Ex.: Comparative Example

Example 6

Adsorptivity Test of Dyes

The adsorptivities of Congo Red ($C_{32}H_{22}N_6O_6S_2Na_2$), Sudan Black B (Sudanschwarz B) and Titan Yellow ($C_{28}H_{19}N_5O_6S_4Na_2$) of Wako Pure Chemical Industries, Ltd., C. I. Direct Black 51 ($C_{27}H_{17}N_5O_8Na_2$) of Hodogaya Chemical Co., Ltd. and Green FLB of Dainichiseika Color & Chemicals Mfg. Co., Ltd. were examined.

(i) Preparation of Sample

Example 6-A

The constitution of the raw materials was the same as that of the sample of Example 4-B. However, heat treatment conditions were different as described below. Conditions for the autoclave treatment were 180° C. and 20 hours. Further, prior to the autoclave treatment, a heat treatment was conducted at 100° C. for 2 hours under open conditions.

Example 6-B

The sample prepared in Example 4-C was used.

Example 6-C

The sample prepared in Example 4-D was used.

Example 6-D

The sample prepared in Example 1-H was used.

Example 6-E

The sample prepared in Example 1-I was used.

Example 6-F

The sample prepared in Example 1-J was used.

Example 6-G

The sample prepared in Example 1-K was used.

Example 6-H

The sample prepared in Example 1-L was used.

Example 6-I

The sample prepared in Example 1-M was used.

Example 6-J

The sample prepared in Example 1-P was used.

Example 6-K

The sample prepared in Example 1-Q was used.

Comparative Example 5

Activated carbon which was generally used as an adsorbent was used.

(ii) Test Method 10 mg of the dye was added to 100 ml of pure water and fully agitated, and 2 g of the sample was added. After the solution was agitated for 15 hours continuously, the supernatant liquid was extracted to make an analysis of the concentration of the dye by a spectrophotometric method.

(iii) Results

The dye adsorption rates are shown in the following Table 5.

The results of Examples 6-A to 6-K demonstrate that the organic acid anion containing aluminum salt hydroxide particles of the present invention adsorb acid dyes, direct dyes, basic dyes, reactive dyes and the like well. Consequently, the organic acid anion containing aluminum salt hydroxide particles of the present invention are useful as a coloration aid, a pigment and a carrier for organic polymers such as resins.

machine FS120S18ASE of NISSEI PLASTIC INDUSTRIAL CO., LTD., and the percentage of elongation of the sample piece was measured. The measurement results are shown in Table 6.

(iii) Results

The following Table 6 demonstrates that the percentage of elongation of the resin into which the organic acid anion containing aluminum salt hydroxide particles of the present invention were kneaded was at least 10 times higher than the conventionally known additive.

TABLE 5

| | Dye Adsorption Rate (%) | | | | |
|---|---|---|---|---|---|
| Example | Congo Red | Sudan Black B | Titan Yellow | C.I. Direct Black 51 | Green FLB |
| 6-A | 64.41 | 98.66 | 82.64 | 94.27 | 99.90 |
| 6-B | 99.73 | 97.65 | 99.68 | 100 | 100 |
| 6-C | 99.92 | 92.83 | 99.74 | 100 | 100 |
| 6-D | 75.45 | 98.84 | 88.33 | 95.41 | 99.94 |
| 6-E | 93.21 | 98.45 | 90.21 | 95.66 | 99.88 |
| 6-F | 72.33 | 95.20 | 98.77 | 98.56 | 98.33 |
| 6-G | 88.32 | 93.88 | 96.22 | 99.85 | 98.65 |
| 6-H | 92.45 | 96.55 | 98.88 | 97.55 | 99.55 |
| 6-1 | 87.60 | 95.85 | 99.21 | 100 | 100 |
| 6-J | 84.20 | 96.33 | 99.15 | 99.60 | 99.52 |
| 6-K | 75.22 | 92.31 | 96.54 | 99.65 | 99.36 |
| C. Ex. 5 | 2.42 | 8.64 | 5.74 | 5.0 | 4.85 |

C. Ex.: Comparative Example

Example 7

Elongation Percentage Test of Resin Composition (i) Preparation of Sample 1.435 g of $Na_2SO_4$ was dissolved in 9.8 L (10 mol) of aluminum sulfate $Al_2(SO_4)_3$ solution, and 315 g of oxalic acid was added directly. 26 L of pure water was added under agitation, and the mixed solution was agitated until $Na_2SO_4$ and oxalic acid were dissolved completely. Then, 12 L (40.5 mol) of sodium hydroxide solution was added. After the mixed solution was agitated at room temperature for 1 hour, it was subjected to a hydrothermal treatment at 170° C. for 8 hours. After the hydrothermal treatment, the resulting mixture was filtered and the precipitate was rinsed with water, and dried at 95° C. for 25 hours. As for Comparative Example 6, magnesium hydroxide (KISUMA 5A of Kyowa Chemical Industry Co., Ltd., BET: 5 $m^2/g$) which was widely used generally as an additive was used as a sample.

(ii) Test Method 60 wt % of the sample, 39.8 wt % of impact resistant grade polypropylene resin, 0.1 wt % of antioxidant DLTP (DLTP: Dilauryl Thiodipropionate of Yoshitomi Seiyaku Co., Ltd.) and 0.1 wt % of antioxidant IR1010b (IR1010: product of Irganox Ciba Specialty Chemicals) were mixed together. From the obtained resin composition, a sample piece for a tensile test was prepared by use of an injection molding

TABLE 6

| | Components | Composition (%) | Yield Point Tensile Strength (kgf/mm$^2$) | Percentage of Elongation (%) |
|---|---|---|---|---|
| Example 7 | Impact Resistant Grade Polypropylene | 39.8 | 1.52 | 380 |
| | Organic Acid Anion Containing Aluminum Salt Hydroxide Particles | 60.0 | | |
| | DLTP | 0.1 | | |
| | IR1010 | 0.1 | | |
| Comparative Example 6 | Impact Resistant Grade Polypropylene | 39.8 | 190 | 30 |
| | Magnesium Hydroxide | 60.0 | | |
| | DLTP | 0.1 | | |
| | IR1010 | 0.1 | | |

Example 8
Whitening Test of Resin Composition (i) Preparation of Sample

For a whitening test, the organic acid anion containing aluminum salt hydroxide particles containing propylene piece prepared in Example 7 was used. Meanwhile, for Comparative Example 7, the same polypropylene piece as that used in Comparative Example 6 to which magnesium hydroxide that was generally used as an additive had been added was used.

(ii) Test Method

The test piece was charged into a constant-temperature pure-water tank of 24° C., and carbon dioxide gas was fed into the tank from a carbon dioxide gas cylinder at a rate of 1.0 L/min for 48 hours to observe whitening of the surface of the resin visually and analyze the concentration of metal ions in the solution.

(iii) Results

The obtained results are shown in the following Table 7. While surface whitening was clearly seen on magnesium hydroxide (KISUMA 5A of Kyowa Chemical Industry Co., Ltd., BET: 5 m²/g) containing polypropylene piece (Comparative Example 7), surface whitening was not seen on the organic acid anion containing aluminum salt hydroxide particles containing propylene piece (Example 8). Further, in the former, elution of metal into the solution was seen, while in the latter, it was not seen.

This result demonstrates that the organic acid anion containing aluminum salt hydroxide particles of the present invention are stable even if added to a resin and do not induce a phenomenon such as whitening.

TABLE 7

| | Solvent | Measurement Temperature (° C.) | Testing Time (hr) | Feed Rate of $CO_2$ | pH of Solution (room temperature) | Amount of Eluted Metal (ppm) |
|---|---|---|---|---|---|---|
| Example 8 | Pure Water | 24 | 48 | 1.0 L/min | 4.0 | 0.05> |
| C. Ex. 7 | Pure Water | 24 | 48 | 1.0 L/min | 4.51 | 13.6 |

C. Ex.: Comparative Example

Example 9

Infrared Radiation Absorbability Test

Figure 20:
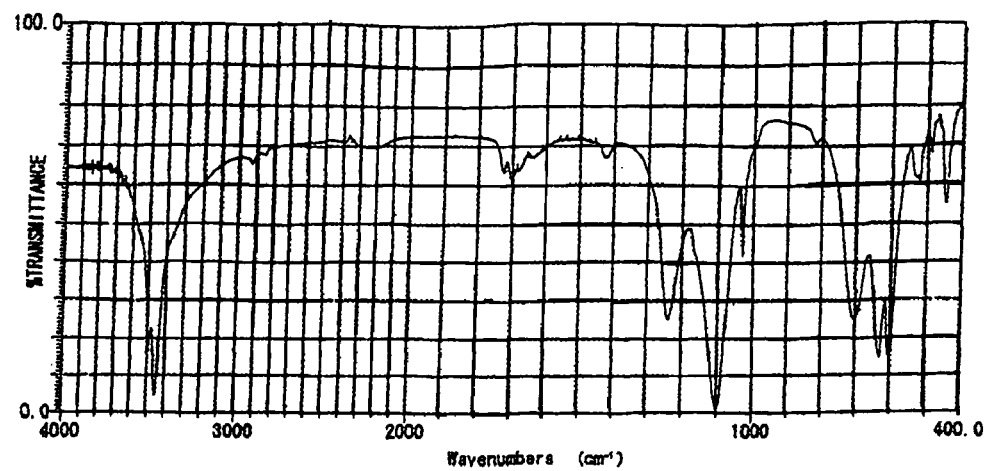
FIG. 20 is an IR spectrum of the organic acid anion containing aluminum salt hydroxide particles of Example 9, wherein the horizontal axis represents wavenumbers (cm) and the vertical axis represents reflectance (%).
Figure 21:
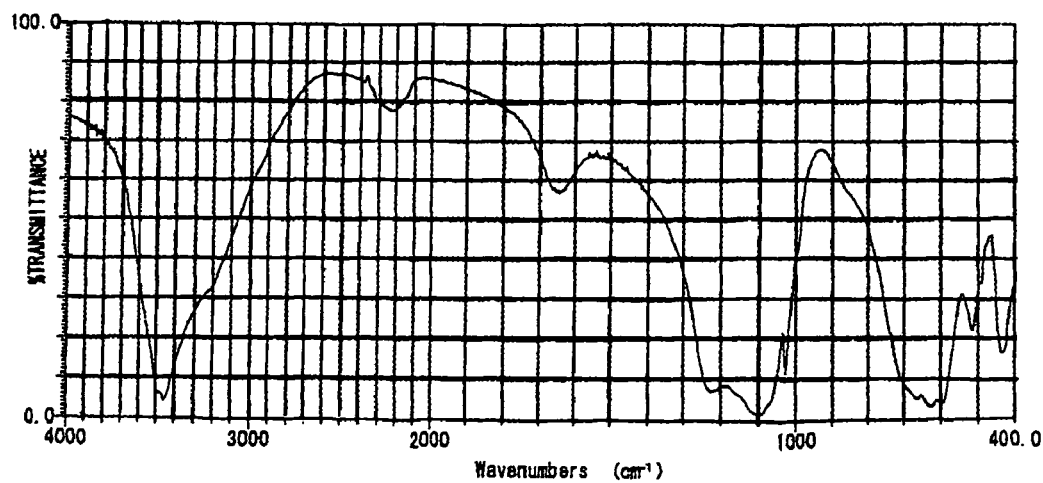
FIG. 21 is an IR spectrum of the organic acid anion containing aluminum salt hydroxide particles of Example 9, wherein the horizontal axis represents wavenumbers (cm) and the vertical axis represents reflectance (%).

As a result of analyzing IR for $NaAl_3(SO_4)_2(OH)_6$ prepared in Examples 1-B and 1-C in accordance with a KBr pellet method, the results shown in FIGS. 20 and 21 were obtained. It is obvious from these results that an IR absorption band exists around 1,600 to 1,800 cm$^{-1}$ (wavelength: 10 to 14 μm) and $NaAl_3(SO_4)_2(OH)_6$ is useful as an infrared absorber.

Example 10

Figure 22:
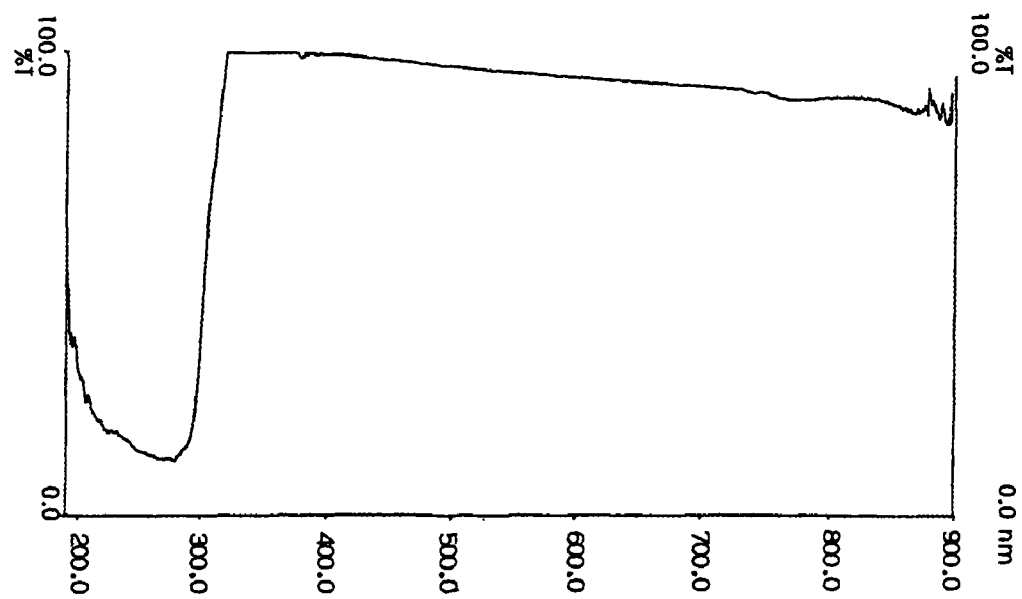
FIG. 22 is an ultraviolet to visible light reflectance spectrum of the organic acid anion containing aluminum salt hydroxide particles of Example 10-A, wherein the horizontal axis represents wavelengths (nm) and the vertical axis represents reflectance (%).

Measurement of Ultraviolet to Visible Reflectance Spectrum (i) Preparation of Sample Example 10-A The absorption spectrum of the sample synthesized in Example 1-H is shown in FIG. 22.

Example 10-B

Figure 23:
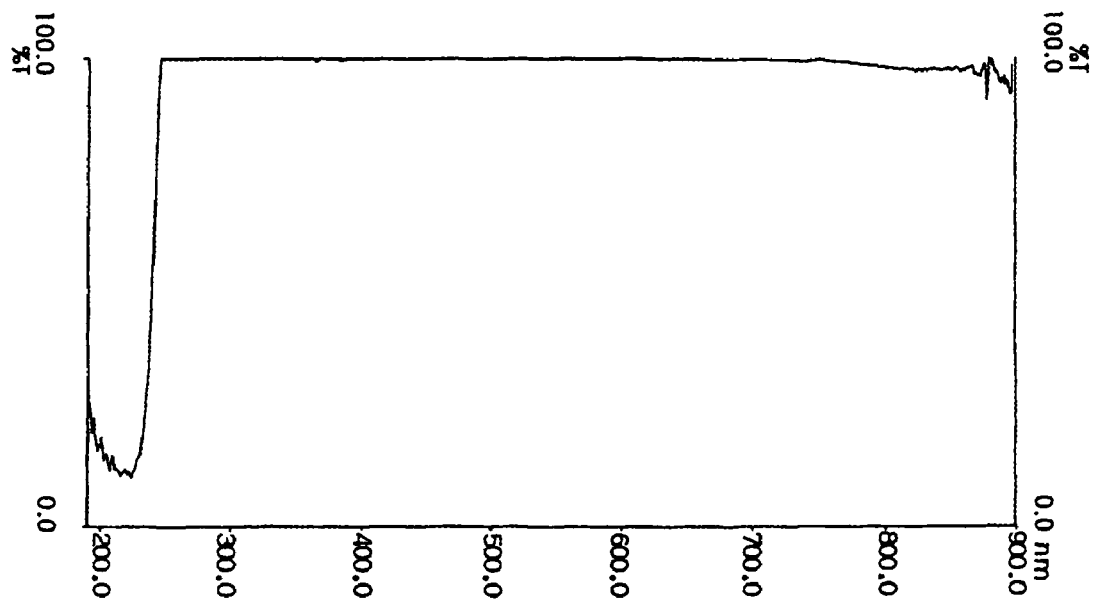
FIG. 23 is an ultraviolet to visible light reflectance spectrum of the organic acid anion containing aluminum salt hydroxide particles of Example 10-B.

The absorption spectrum of the sample synthesized in Example 1-J is shown in FIG. 23.

Example 10-C

Figure 24:
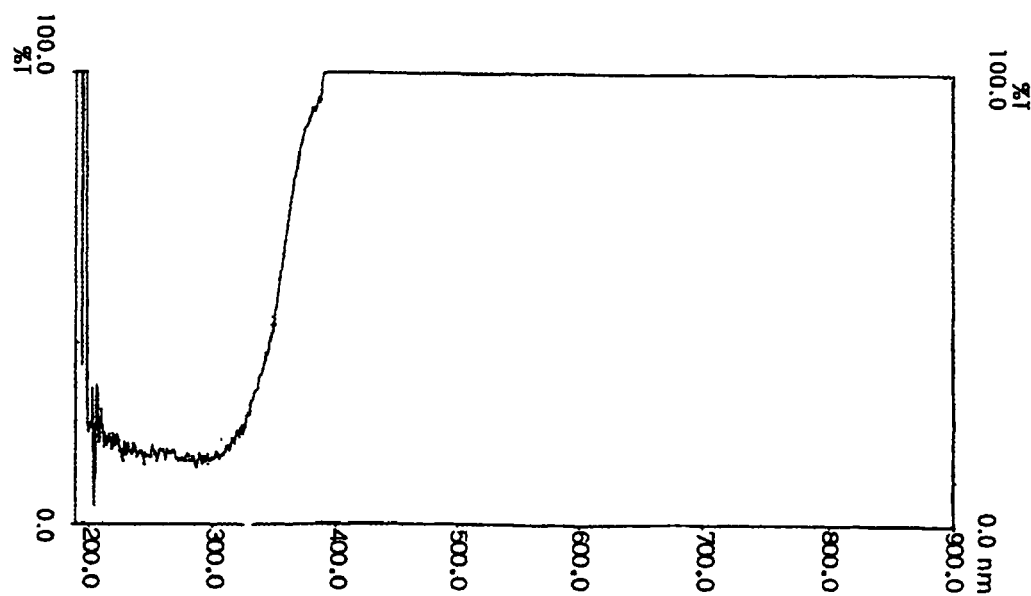
FIG. 24 is an ultraviolet to visible light reflectance spectrum of the organic acid anion containing aluminum salt hydroxide particles of Example 10-C.

The absorption spectrum of the sample synthesized in Example 2-A is shown in FIG. 24.

(ii) Test Method

A reflectance spectrum was measured on a sample piece prepared by molding sample power into a disk having a size of ϕ40×2 mm by use of a spectrophotometer.

(iii) Result

The organic acid anion containing aluminum salt hydroxide particles of the present invention have an absorption band in an ultraviolet region of 200 to 380 nm and are useful as an ultraviolet absorber.

Example 11

Differential Thermal Analysis Test

Figure 26:
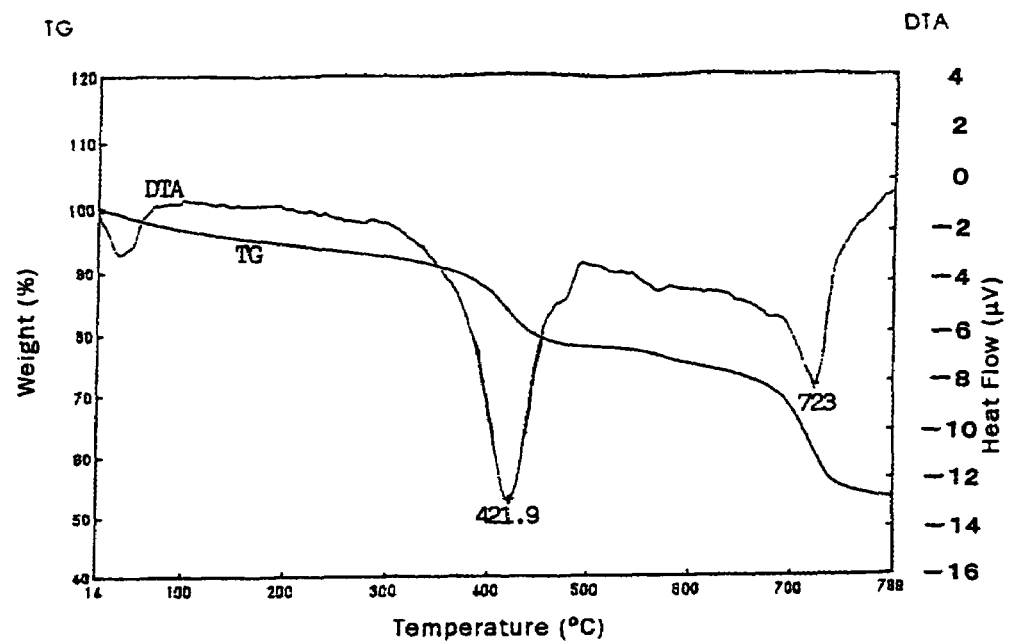
FIG. 26 is a differential thermal analysis diagram of the organic acid anion containing aluminum salt hydroxide particles of Example 11, wherein the horizontal axis represents wavenumbers ($cm^{-1}$) and the vertical axis represents weights (%).
Figure 27:
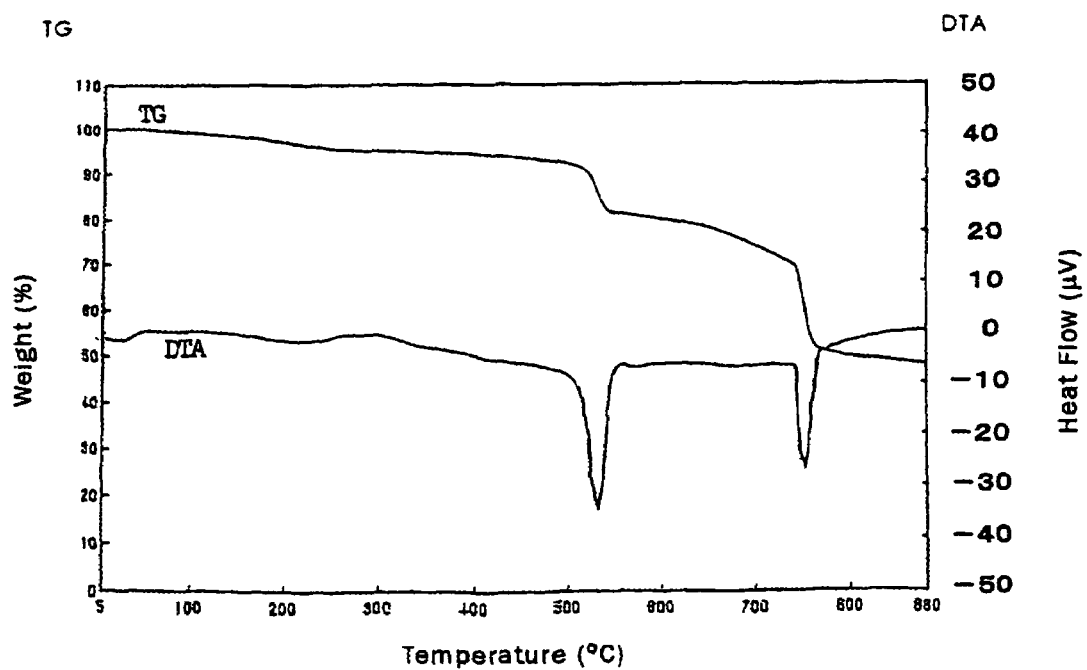
FIG. 27 is a differential thermal analysis diagram of the organic acid anion containing aluminum salt hydroxide particles of Example 11, wherein the horizontal axis represents wavenumbers ($cm^{-1}$) and the vertical axis represents weights (%).
Figure 28:
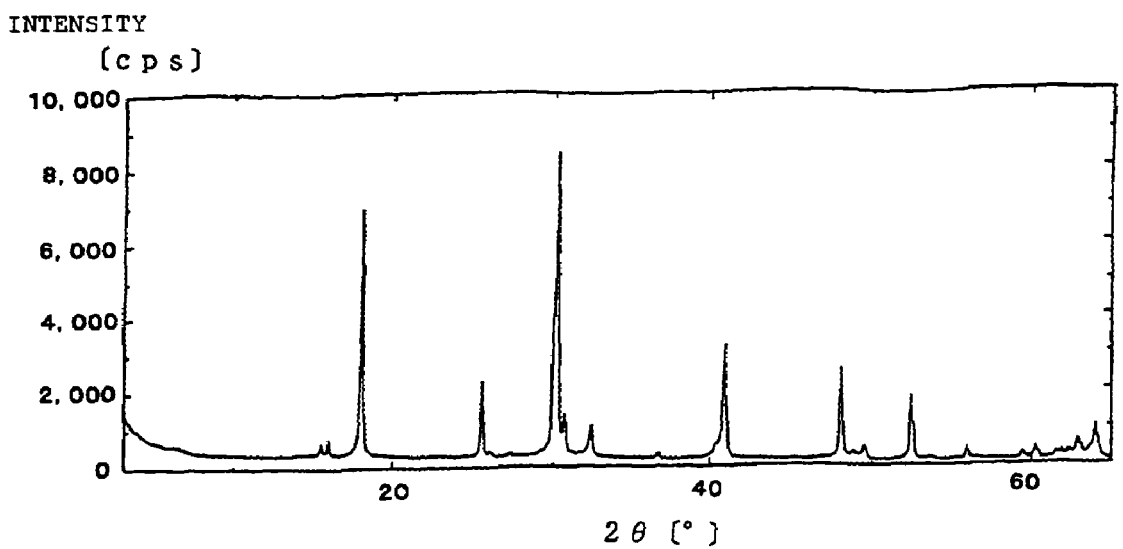
FIG. 28 is an X-ray diffraction diagram of the organic acid anion containing aluminum salt hydroxide particles of Example 14.
Figure 29:
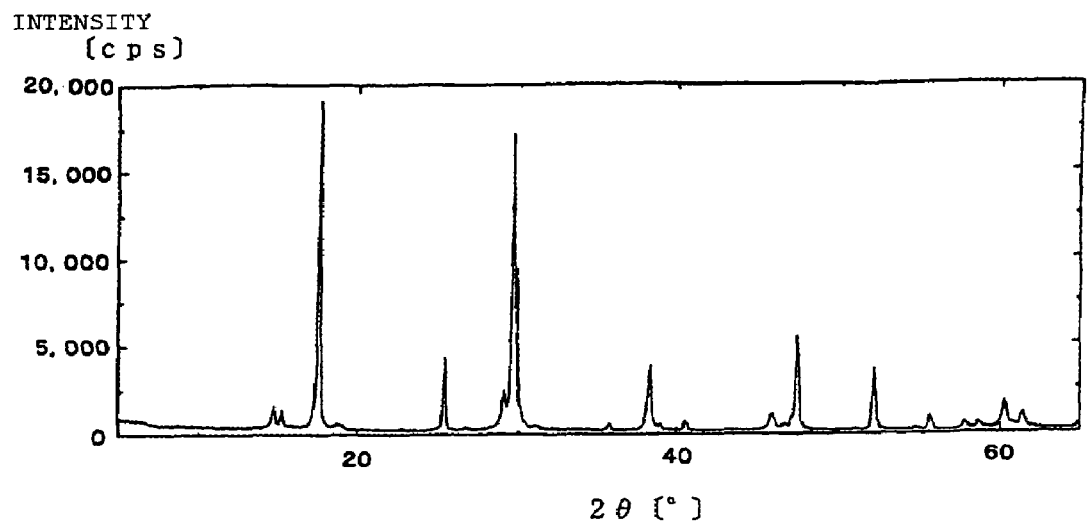
FIG. 29 is an X-ray diffraction diagram of the organic acid anion containing aluminum salt hydroxide particles of Example 14.
Figure 30:
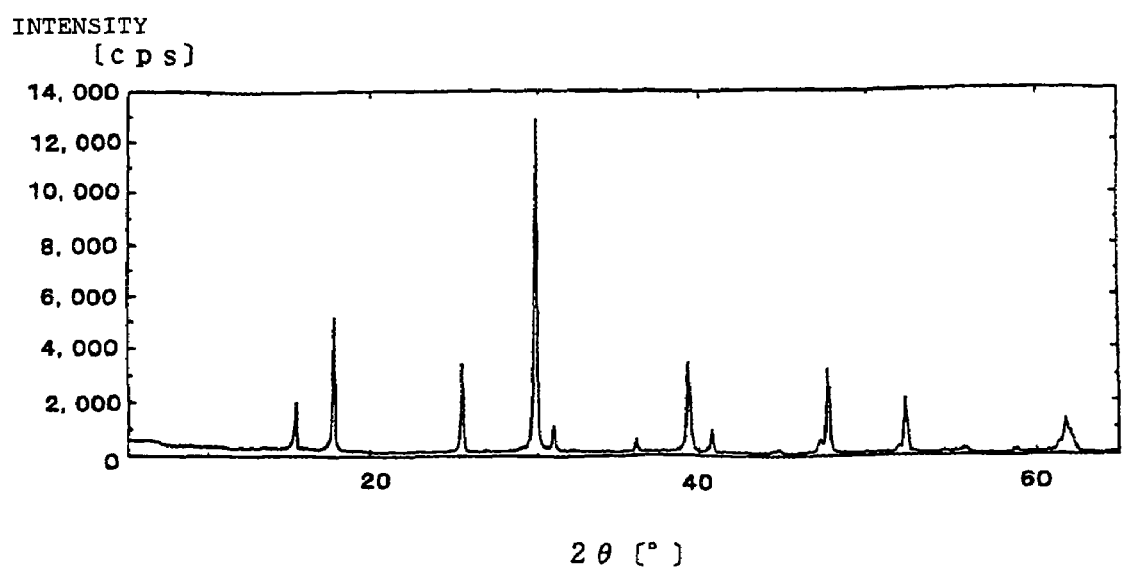
FIG. 30 is an X-ray diffraction diagram of the organic acid anion containing aluminum salt hydroxide particles of Example 14.
Figure 31:
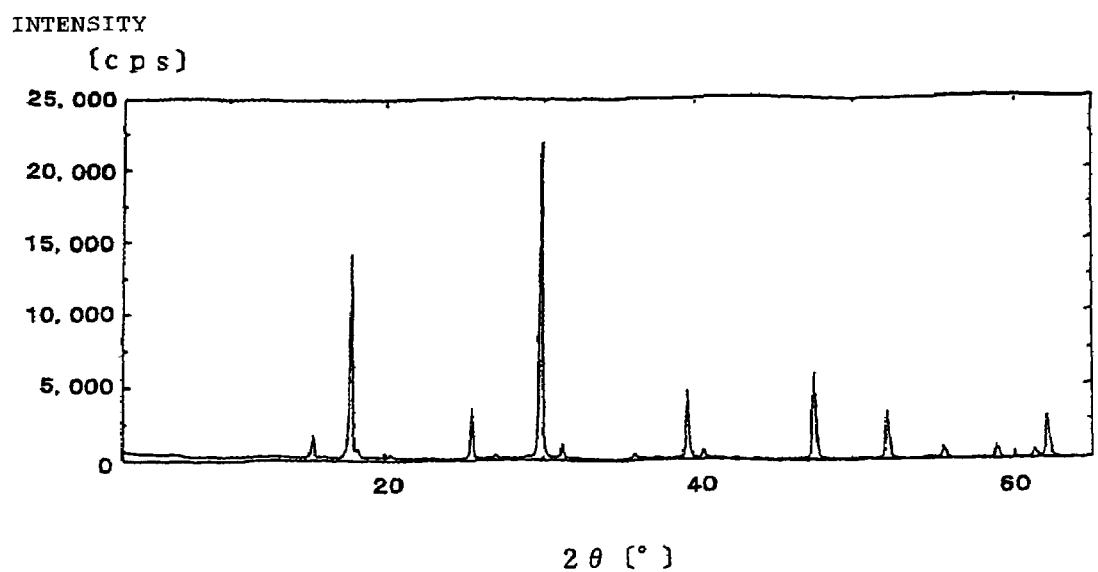
FIG. 31 is an X-ray diffraction diagram of the organic acid anion containing aluminum salt hydroxide particles of Example 14.
Figure 32:
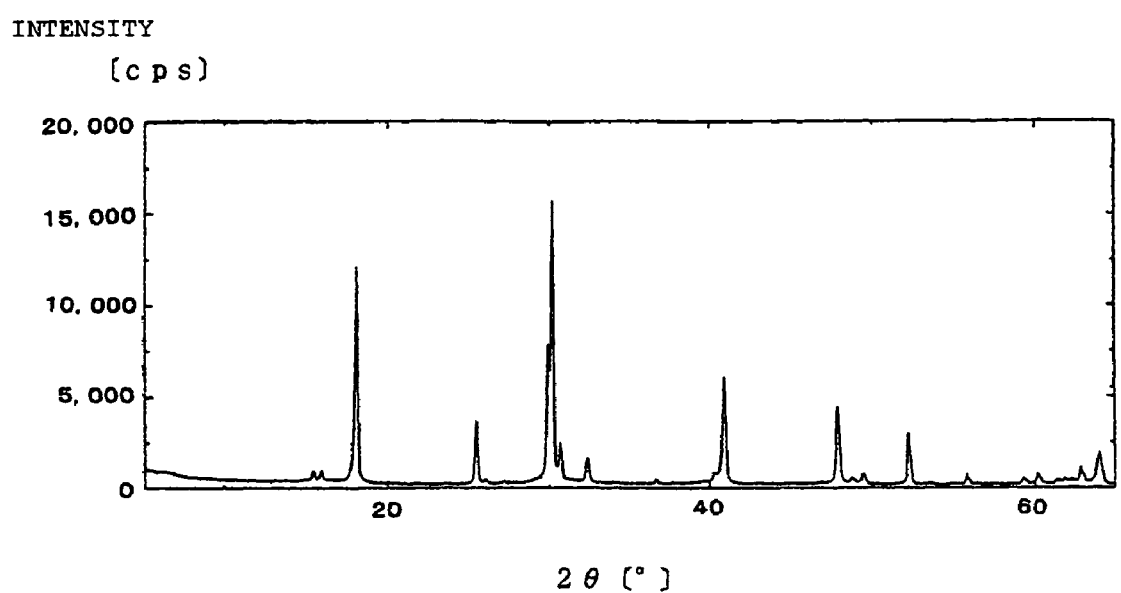
FIG. 32 is an X-ray diffraction diagram of the organic acid anion containing aluminum salt hydroxide particles of Example 14.

As a result of making a differential thermal analysis on $NaAl_3(SO_4)_2(OH)_6$ prepared in Examples 1-B and 1-C, the results shown in FIGS. 26 and 27 were obtained. Both samples were thermally stable up to 400° C. or higher.

Example 12

Relationship between Reaction Conditions and Particle Diameter

The results of measuring the particle diameters of organic acid anion containing aluminum salt hydroxide particles to be produced when the ratio between the rate of addition of alkali hydroxide to be added and the concentration of sulfate was changed in production of the organic acid anion containing aluminum salt hydroxide particles of the present invention by a laser diffraction method are shown in Table 8. Table 8 shows that the particle diameters of the organic acid anion containing aluminum salt hydroxide particles depend on the concentration ratio between alkali hydroxide and sulfate at the time of production reaction.

TABLE 8

| | Treatment Conditions | |
|---|---|---|
| Particle Diameters | Concentration Ratio $Al_2(SO_4)_3$/NaOH in initial stage of Reaction | Temperature and Time for Autoclave Treatment |
| Not Larger Than 0.5 μm | Not Lower Than 0.14 | 95 to 250° C., 2.0 to 20.0 hr |
| 0.5 to 1.0 μm | Not Higher Than 0.14 | 95 to 250° C., 2.0 to 20.0 hr |
| 1.0 to 2.0 μm | Not Higher Than 0.125 | 95 to 250° C., 2.0 to 20.0 hr |
| Not Smaller Than 2.0 μm | Not Higher Than 0.07 | 95 to 250° C., 2.0 to 20.0 hr |

Meanwhile, the results of observing the particle shapes of organic acid anion containing aluminum salt hydroxide particles to be produced when the kind of organic acid to be added, reaction conditions and the reaction molar ratio were varied, by use of an SEM, are shown in Table 9. Table 9 shows that the shapes of the particles to be produced heavily depend on the kind and amount of the organic acid to be added (molar ratio of organic acid to aluminum sulfate: [organic acid]/[aluminum sulfate]) and the reaction temperature.

For *1, *2 and *3 in the table, reaction conditions were different as follows.

TABLE 9

| Organic Acid | Monovalent Ion | | | |
|---|---|---|---|---|
| | Na+ | K+ | NH4+ | H3O+ |
| Oxalic Acid | Disk*1/Pair*2/ Hexagonal Plate*3 | Sphere | Sphere | Rectangular Parallelepiped |
| Citric Acid | Sphere | Sphere | Sphere | Rectangular Parallelepiped |
| Citrate | Sphere | Sphere | Sphere | Rectangular Parallelepiped |
| Tartaric Acid | Rice Grain | Rice Grain | Rice Grain | Rectangular Parallelepiped |
| Tartrate | Sphere | Sphere | Sphere | Rectangular Parallelepiped |
| DL-malic Acid | Sphere | Sphere | Sphere | Rectangular Parallelepiped |
| Gallic Acid | Sphere | Sphere | Sphere | Rectangular Parallelepiped |
| DL-glyceric Acid | Cylinder | Cylinder | Cylinder | Rectangular Parallelepiped |
| L-lactic Acid | Rectangular Parallelepiped | Rectangular Parallelepiped | Rectangular Parallelepiped | Rectangular Parallelepiped |
| Oxalic Acid · Tartaric Acid | Sphere | Sphere | Sphere | Rectangular Parallelepiped |

*1 The molar ratio was 1/4 ≦ [organic acid]/[aluminum sulfate], and the heating reaction was carried out at 150 to 200° C.
*2 The molar ratio was 1/20 ≦ [organic acid]/[aluminum sulfate] < 1/8, and the heating reaction was carried out at 150 to 200° C. for 2 hours.
*3 The molar ratio was 1/8 ≦ [organic acid]/[aluminum sulfate] < 1/4, and the heating reaction was carried out at 150 to 200 ° for 2 hours.

Example 13

Evaluation of Optical Properties (i) Preparation of Sample

Example 13-A

After the organic acid anion containing aluminum salt hydroxide particles synthesized in Example 1-B were mixed in a mixing proportion of 0.1 parts by weight per 100 parts by weight of low-density polyethylene (UF240), the mixture was melt-kneaded at about 180° C. by use of an extruder to prepare pellets. By use of the pellets, a film having a thickness of 100 μm was prepared at about 200° C. by a T-die method and used as a test piece.

Comparative Example 8

After the alunite type compound particles synthesized in Comparative Example 1 were mixed in a mixing proportion of 0.1 parts by weight per 100 parts by weight of low-density polyethylene (UF240), the mixture was melt-kneaded at about 180° C. by use of an extruder to prepare pellets as in Example 13-A. By use of the pellets, a film having a thickness of 100 μm was prepared at about 200° C. by a T-die method and used as a test piece.

Comparative Example 9

After titanium oxide (ST-01: ISHIHARA SANGYO KAISHA, LTD.) was mixed in a mixing proportion of 0.2 parts by weight per 100 parts by weight of low-density polyethylene (UF240), the mixture was melt-kneaded at about 180° C. by use of an extruder to prepare pellets as in Example 13-A. By use of the pellets, a film having a thickness of 100 μm was prepared at about 200° C. by a T-die method and used as a test piece.

Comparative Example 10

A low-density polyethylene (UF240) with no mixture was molten at about 180° C. by use of an extruder to prepare pellets. By use of the pellets, a film having a thickness of 100 μm was prepared at about 200° C. by a T-die method and used as a test piece.

(ii) Test Method

Transmittance and haze were measured by use of a haze meter (TC-H3DP: Nippon Denshoku Industries Co., Ltd.)

(iii) Results

Figure 25:
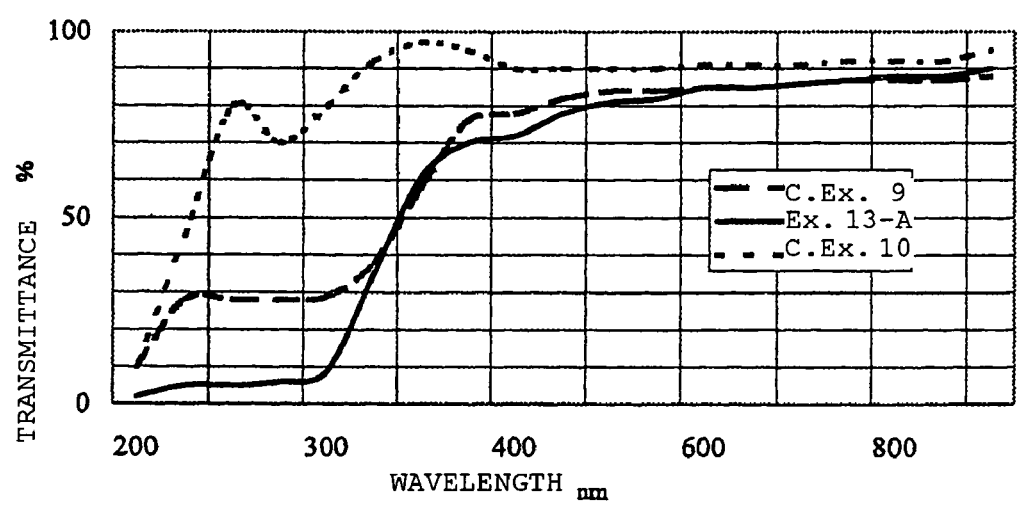
FIG. 25 is a light transmission spectrum of a low-density polyethylene film which contains the organic acid anion containing aluminum salt hydroxide particles of Example 13-A.

The light transmission spectrum is shown in FIG. 25, and the measurement results of the total light transmittance and haze are shown in the following Table 10. Differences in the optical properties due to a difference in thickness were corrected by use of the Lambert-Beer formula in terms of 100 μm. It can be understood from Table 10 that the organic acid anion containing aluminum salt hydroxide particles of the present invention show high transmittance and thin haze even if added to a resin and therefore do not impair the optical properties of a transparent resin in particular.

TABLE 10

| | Ex. 13-A | C. Ex. 8 | C. Ex. 9 | C. Ex. 10 |
|---|---|---|---|---|
| Thickness (μm) | 195 | 115 | 112 | 115 |
| Haze (%) | 40.1 | 43.9 | 75.2 | 26.3 |

TABLE 10-continued

|  | Ex. 13-A | C. Ex. 8 | C. Ex. 9 | C. Ex. 10 |
|---|---|---|---|---|
| Transmittance | 89 | 89.1 | 85.1 | 90 |
| Haze (%) (in terms of 100 μm) | 23.1 | 39.5 | 71.2 | 23.3 |

Ex.: Example C. Ex.: Comparative Example

Example 14

Measurement of Refractive Index (i) Preparation of Sample

Example 14-A

The result of measuring the refractive index of the sample synthesized in Example 1-B is shown in Table 11.

Example 14-B

The result of measuring the refractive index of the sample synthesized in Example 1-C is shown in Table 11.

Example 14-C

The result of measuring the refractive index of the sample synthesized in Example 1-E is shown in Table 11.

Example 14-D

The result of measuring the refractive index of the sample synthesized in Example 1-F is shown in Table 11.

Example 14-E

The result of measuring the refractive index of the sample synthesized in Example 1-O is shown in Table 11.

Example 14-F

The result of measuring the refractive index of the sample synthesized in Example 2-A is shown in Table 11.

Comparative Example 11

The result of measuring the refractive index of the sample synthesized in Comparative Example 1 is shown in Table 11.

(ii) Test Method

The refractive indices were measured in accordance with a method which will be described later.

(iii) Results

It is understood from the following Table 11 that the organic acid anion containing aluminum salt hydroxide particles of the present invention can adjust the refractive index in a wide range of 1.49 to 1.55 according to the kind or other factors of the organic acid contained in the particles and the resin to be added and are useful for a resin which requires transparency in particular.

TABLE 11

| Example | Average Particle Diameter (μm) | Refractive Index |
|---|---|---|
| 14-A | 0.40 | 1.52 |
| 14-B | 1.36 | 1.49 |
| 14-C | 2.44 | 1.52 |
| 14-D | 0.61 | 1.52 |
| 14-E | 3.05 | 1.55 |
| 14-F | 0.55 | 1.55 |
| C. Ex. 11 | 1.64 | 1.52 |

C. Ex.: Comparative Example

Example 15

Analysis of Component

The results of analyzing the components of the organic acid anion containing aluminum salt hydroxide particles of the present invention by use of an atomic absorption spectrophotometer are shown in the following Tables 12-1 and 12-2.

Example 15-A

The result of analyzing the components of the sample synthesized in Example 1-A is shown in Table 12-1.

Example 15-B

The result of analyzing the components of the sample synthesized in Example 1-B is shown in Table 12-1.

Example 15-C

The result of analyzing the components of the sample synthesized in Example 1-C is shown in Table 12-1.

Example 15-D

The result of analyzing the components of the sample synthesized in Example 1-D is shown in Table 12-1.

Example 15-E

The result of analyzing the components of the sample synthesized in Example 1-E is shown in Table 12-1.

Example 15-F

The result of analyzing the components of the sample synthesized in Example 1-H is shown in Table 12-1.

Example 15-G

The result of analyzing the components of the sample synthesized in Example 1-I is shown in Table 12-2.

Example 15-H

The result of analyzing the components of the sample synthesized in Example 1-J is shown in Table 12-2.

Example 15-I

The result of analyzing the components of the sample synthesized in Example 1-K is shown in Table 12-2.

Example 15-J

The result of analyzing the components of the sample synthesized in Example 1-L is shown in Table 12-2.

Example 15-K

The result of analyzing the components of the sample synthesized in Example 1-Q is shown in Table 12-2.

Example 15-L

The result of analyzing the components of the sample synthesized in Example 1-R is shown in Table 12-2.

TABLE 12-1

| Content (%) | Ex. 15-A | Ex. 15-B | Ex. 15-C | Ex. 15-D | Ex. 15-E | Ex. 15-F |
|---|---|---|---|---|---|---|
| $Al^{3+}$ | 18.99 | 16.66 | 18.11 | 18.88 | 20.79 | 20.01 |
| $SO_4^{2-}$ | 46.81 | 44.03 | 46.35 | 44.96 | 48.37 | 45.74 |
| $Na^+$ | 6.32 | 6.18 | 6.16 | 0.01 | 0.14 | 6.00 |
| $K^+$ | 0.02 | 0.03 | 0.02 | 10.95 | 0.01 | 0.10 |
| $NH_4^+$ | 4.10 | — | — | — | — | — |
| $OH^-$ | 27.59 | 30.41 | 28.12 | 23.63 | — | 25.00 |
| $H^+$ | — | — | — | — | — | — |
| $C_2O_4^{2-}$ | — | — | — | — | — | 2.87 |
| $C_4H_4O_6^{2-}$ | — | — | — | — | — | — |
| $C_4H_4O_5^{2-}$ | — | — | — | — | — | — |
| $C_6H_5O_7^{3-}$ | — | — | — | — | — | — |
| $H_2O$ | 0.24 | 2.69 | 1.20 | 1.52 | 0.24 | 0.24 |

Ex.: Example

TABLE 12-2

| Content (%) | Ex. 15-G | Ex. 15-H | Ex. 15-I | Ex. 15-J | Ex. 15-K | Ex. 15-L |
|---|---|---|---|---|---|---|
| $Al^{3+}$ | 19.49 | 19.67 | 19.06 | 18.55 | 21.11 | 19.31 |
| $SO_4^{2-}$ | 45.00 | 43.84 | 46.61 | 43.09 | 49.81 | 49.70 |
| $Na^+$ | 5.81 | 4.77 | 5.60 | — | 0.18 | 0.11 |
| $K^+$ | — | — | — | 9.24 | — | — |
| $NH_4^+$ | — | — | — | — | — | 4.26 |
| $OH^-$ | 23.65 | 23.31 | 22.70 | 22.70 | 25.75 | 21.99 |
| $H^+$ | — | — | — | — | 0.26 | — |
| $C_2O_4^{2-}$ | — | — | — | — | 2.85 | 2.68 |
| $C_4H_4O_6^{2-}$ | — | 8.23 | — | — | — | — |
| $C_4H_4O_5^{2-}$ | — | — | 3.83 | — | — | — |
| $C_6H_5O_7^{3-}$ | 5.83 | — | — | 6.34 | — | — |
| $H_2O$ | 0.23 | 0.19 | 2.20 | 0.09 | 0.05 | 1.96 |

Ex.: Example

Example 16

X-ray Diffraction

As a result of making an X-ray diffraction analysis on the organic acid anion containing aluminum salt hydroxide particles of the present invention, i.e.,
$NaAl_3(SO_4)_2(OH)_6$ (sample of Example 1-F),
$NH_4Al_3(SO_4)_2(OH)_6$ (sample of Example 1-A),
$KAl_3(SO4)_2(OH)_6$ (sample of Example 1-D), $HAl_3(SO_4)_2(OH)_6$ (sample of Example 1-E) and
$Na_{1.11}Al_{2.98}(SO_4)_{1.96}(C_2O_4)_{0.201}(OH)_{5.73} \cdot 0.8H_2O$ (sample of Example 1-G), X-ray diffraction diagrams of FIGS. 28, 29, 30, 31 and 32 were obtained. These X-ray diffraction diagrams demonstrate that the alunite compounds of the present invention have different patterns and intensity ratios, i.e., different composition ratios, from those of conventionally known synthetic aluminum salt hydroxide particles.

Descriptions of Methods and Apparatuses Used for Analyses and Tests

Methods and apparatuses used for the analyses and the tests will be described hereinafter.

(1) Refractive Index

Method: 5 mg of sample powder was added to 5 ml of organic solvent and dispersed for 10 minutes by ultrasound, and a transparent portion was spread on the main prism surface in the form of a thin film to determine the refractive index.

Apparatus: Abbe refractometer 1T (ATAGO Co., Ltd.)

(2) SEM

Method: accelerating voltage=15 KV, operating distance=10 mm, magnification=2,000-fold, 10,000-fold, 20,000-fold Apparatus: S-3000N (Hitachi, Ltd.)

(3) Differential Thermal Analysis

Method: air atmosphere=100 ml/min; reference sample=α-alumina; temperature increasing rate=10° C./min Apparatus: Thermal Analysis Station TAS100; TG8110 (Rigaku Corporation)

(4) Analysis of IR

Method: KBr pellet method

Apparatus: Fourier transform infrared spectrophotometer FT-710 (HORIBA Ltd.)

(5) Analyses of Particle Diameter and Particle Size Distribution (by Laser Diffraction Method)

Method: Sample powder was added to 0.2% sodium hexametaphosphate (concentration: 1 wt %) and dispersed for 3 minutes by ultrasound to measure the particle diameter.

Apparatus: LA-910 (HORIBA Ltd.)

(6) Analysis of Specific Surface Area BET

Method: three-point method

Apparatus: NOVA2000 high-speed specific surface area/pore distribution measuring apparatus (Yuasa Ionics Inc.)

(7) Analysis of X-Ray Diffraction

Method: Cu-Kα, angle (θ): 5 to 65, step: 0.02, scanning speed: 4, tube voltage: 40 kV, tube current: 20 mV Apparatus: RINT2200V X-ray diffraction system (Rigaku Corporation)

(8) Dye Adsorption Test

Method: 2 g of sample and 10 mg of dye were added to 150 ml of pure water, fully agitated, and the concentration of the dye at the beginning and after 15 hours was analyzed.

Adsorption Rate=(a−b)/a×100(%)

a: initial concentration of dye in solution b: concentration of dye after 15-hour adsorption Apparatus: 150-20 spectrophotometer and data processor of Hitachi, Ltd.

(9) Analysis of Oxygen Content

Apparatus: JSM6300 SCANNING MICROSCOPE

(10) Malodorous Gas Adsorption Test

Ammonia $NH_3$

Standard Gas Concentration: 197 ppm

1 L of ammonia was introduced into 50 ml of pure water, and the residual gas was measured by the calibration curve of pH.

Trimethylamine $(CH_3)_3N$

Standard Gas Concentration: 198 ppm

Introduced Amount: 1.0 ml
Temperature of Sample Vaporizing Chamber: 130° C.
Column: Diglycerol+TEP+KOH 15+15+2% Chromosorb W 80/100 AW-DMCS 3.1 m×3.2 mm
Temperature of Column: 60° C. (constant)
Carrier Gas: $N_2$
Flow Rate: 50 ml/min
Pressure: 130 kPa
Detector: FID
Hydrogen Gas Pressure: 50 kPa
Air Pressure: 50 kPa
Temperature of Detector: 130° C.
iso-valeric acid $(CH_3)_2CHCOOH$
Standard Gas Concentration: 20.0 ppm
Introduced Amount: 1.0 ml
Temperature of Sample Vaporizing Chamber: 250° C.
Column: DB-WAX 30 m×0.32 mm
Temperature of Column: 220° C. (constant)
Carrier Gas: He
Flow Rate: 2.3 ml/min
Pressure: 50 kPa
Detector: FID
Hydrogen Gas Pressure: 50 kPa
Air Pressure: 50 kPa
Temperature of Detector: 250° C.

(11) Method for Measuring Percentage of Elongation of Resin
Method: in accordance with the plastic tensile test method (JIS-K7113)
Apparatus: TENSILON/UTM-1-2500 AND SS-207D-UA (TOYO BALDWIN CO., LTD.)

(12) Method for Measuring Water Absorption
Method: Water absorption was measured in accordance with a method conforming to JIS-K6911 5.26.1.
Apparatus: constant-temperature constant-moisture tank AGX-326 of ADVANTECH TOYO CO., LTD.

(13) Measurement of Ultraviolet to Visible Light Reflectance
Apparatus: spectrophotometer 150-20 (Hitachi, Ltd.)

The invention claimed is:

1. Organic acid anion containing aluminum salt hydroxide particles represented by the following general formula (I):

$$M_a[Al_{1-x}M'_x]_b A_z B_y (OH)_n \cdot mH_2O \qquad (I)$$

(wherein M is at least one cation selected from the group consisting of $Na^+$, $K^+$ and $NH^{4+}$, M' is at least one metal cation selected from the group consisting of $Cu^{2+}$, $Zn^{2+}$, $Ni^{2+}$, $Sn^{4+}$, $Zr^{4+}$, $Fe^{2+}$, $Fe^{3+}$ and $Ti^{4+}$, A is at least one organic acid anion based on an organic acid selected from the group consisting of (i) an organic carboxylic acid having 2 to 10 carbon atoms and 1 to 4 carboxyl groups and (ii) an organic oxycarboxylic acid having 2 to 10 carbon atoms and 1 to 4 carboxyl groups, B is at least one inorganic acid anion selected from the group consisting of a sulfate ion, a phosphate ion and a nitrate ion, and a, b, m, n, x, y and z satisfy $0.7 \leq a \leq 1.35$, $2.7 \leq b \leq 3.3$, $0 \leq m \leq 5$, $4 \leq n \leq 7$, $0 \leq x \leq 0.6$, $1.7 \leq y \leq 2.4$, and $0.001 \leq z \leq 0.5$, respectively).

2. The particles according to claim 1, which are represented by the formula (I) wherein a satisfies $0.9 \leq a \leq 1.2$.

3. The particles according to claim 1, which are represented by the formula (I) wherein b satisfies $2.8 \leq b \leq 3.2$.

4. The particles according to claim 1, which are represented by the formula (I) wherein m satisfies $0 \leq m \leq 2$.

5. The particles according to claim 1, which are represented by the formula (I) wherein n satisfies $5 \leq n \leq 6.5$.

6. The particles according to claim 1, which are represented by the formula (I) wherein x satisfies $0 \leq x \leq 0.3$.

7. The particles according to claim 1, which are represented by the formula (I) wherein y satisfies $1.8 \leq y \leq 2.2$.

8. The particles according to claim 1, which are represented by the formula (I) wherein z satisfies $0.01 \leq z \leq 0.4$.

9. The particles according to claim 1, wherein the organic acid anion (A) in the formula (I) is at least one selected from anions based on an oxalic acid, a citric acid, a citrate, a tartaric acid, a tartrate, a DL-malic acid, a gallic acid, a DL-glyceric acid and an L-lactic acid.

10. The particles according to claim 1, wherein $D_{25}$ and $D_{75}$ satisfy $1 < D_{75}/D_{25} < 1.8$ when particle diameters at 25% and 75% values of cumulative particle size distribution curve measured by a laser diffraction method are represented by $D_{25}$ and $D_{75}$, respectively.

11. The particles according to claim 1, which are in the shape of grains, pairs, rectangular parallelepiped, disks (go stones), hexagonal plates, rice grains or cylinders.

12. The particles according to claim 1, having an average particle diameter of 0.1 to 10 μm.

13. The particles according to claim 1, which carry a hydrolysate of a salt of at least one metal selected from the group consisting of Cu, Zn, Ni, Sn, Zr, Fe and Ti, on the surfaces thereof.

14. A method for producing organic acid anion containing aluminum salt hydroxide particles of claim 1, which comprises adding a solution of a hydroxide of an ion selected from the group consisting of $Na^+$, $K^+$ and $NH_4^+$ to a mixed solution comprising an organic acid or organic acid salt selected from the group consisting of (i) an organic carboxylic acid having 2 to 10 carbon atoms and 1 to 4 carboxyl groups, (ii) an organic oxycarboxylic acid having 2 to 10 carbon atoms and 1 to 4 carboxyl groups, and (iii) salts thereof, an inorganic salt of $Al^{3+}$ selected from the group consisting of an aluminum sulfate, an aluminum phosphate and an aluminum nitrate, and a sulfate or nitrate of at least one member selected from the group consisting of $Na^+$, $K^+$ and $NH_4^+$ to cause a heating reaction and produce the organic acid anion containing aluminum salt hydroxide particles of claim 1.

15. The method according to claim 14, wherein the inorganic salt is aluminum sulfate.

16. The method according to claim 14, wherein the heating reaction is carried out at 90 to 250° C.

17. The method according to claim 14, wherein the mixed solution further comprises an inorganic salt of at least one cation selected from the group consisting of $Cu^{2+}$, $Zn^{2+}$, $Ni^{2+}$, $Sn^{4+}$, $Zr^{4+}$, $Fe^{2+}$, $Fe^{3+}$ and $Ti^{4+}$.

18. The method according to claim 17, wherein the heating reaction is carried out at 90 to 250° C.

* * * * *